United States Patent [19]
Van Den Bergh et al.

[11] Patent Number: 5,675,419
[45] Date of Patent: *Oct. 7, 1997

[54] SCATTERED/TRANSMITTED LIGHT INFORMATION SYSTEM

[76] Inventors: Herman Van Den Bergh, Pine Lodge, Lackandarragh, Enniskerry, Wicklow, Ireland; Marvin Lane, 6405 Orange Hill La., Carmichael, Calif. 95608; John Mallon, 2 Dun An Oir, Milford Grange, Castletroy, Limerick, Ireland

[*] Notice: The term of this patent shall not extend beyond the expiration date of Pat. No. 5,471,311.

[21] Appl. No.: 533,019

[22] Filed: Sep. 25, 1995

Related U.S. Application Data

[62] Division of Ser. No. 211,400, filed as PCT/IE92/00012, Sep. 30, 1992, published as WO93/07468, Apr. 15, 1993. Pat. No. 5,471,311.

[30] Foreign Application Priority Data

Oct. 1, 1991 [IE] Ireland ................... 3454/91

[51] Int. Cl.⁶ ............... G01N 21/89; G01N 21/49
[52] U.S. Cl. ............... 356/446; 250/226; 356/407
[58] Field of Search ............... 356/445, 446, 356/407; 250/226

[56] References Cited

U.S. PATENT DOCUMENTS

| | | |
|---|---|---|
| 3,786,266 | 1/1974 | Reid et al. |
| 4,223,680 | 9/1980 | Jobsis. |
| 4,600,105 | 7/1986 | Van Zyl et al. ........... 209/587 |
| 4,950,905 | 8/1990 | Butler et al. |

FOREIGN PATENT DOCUMENTS

| | | |
|---|---|---|
| 0231027 | 8/1987 | European Pat. Off. |
| 60-31041 | 2/1985 | Japan. |
| 2098725 | 11/1982 | United Kingdom. |

*Primary Examiner*—Vincent P. McGraw
*Attorney, Agent, or Firm*—Young & Thompson

[57] ABSTRACT

In an information gathering system especially suited to the monitoring of vegetable products in sorting apparatus, a light beam (23) is directed by a scanning source such as a laser (11) at the surface of an object (2) such as a tomato moving in the direction x—x through a scanning zone. The scanning operation is conducted in the y—y direction. Directly reflected light returned from the surface of the object (2) along a path (17) extending from light beam target region (12) is sensed by a line detector (14), which provides an output signal indicative of the level, of the directly reflected light. Light entering the material of the organic product (2) is subjected to a light scattering or diffusing process within the material of the product, so that at least a region (13) of the surface of the product (12) surrounding the target zone (12) of light beam (23) becomes lit-up or illuminated from within. Further photosensitive line detectors (15) and (16) located one to each side of reflected light detector (14) monitor the levels of light emanating from this illuminated zone (13) surrounding light beam target zone (12) and reaching the detectors (15) and (16) along paths (18) and (19) respectively. Comparison of the relative levels of the directly reflected light and emanating light signals enables information to be derived as to surface and subsurface defects on or in the product (2). The use of suitable logic circuitry enables rejection of defective product in response to the information provided by the light signals.

21 Claims, 16 Drawing Sheets

SCATTERED/TRANSMITTED LIGHT INFORMATION SYSTEM

This application is a divisional of application Ser. No. 08/211,400, filed as PCT/IE92/00012, Sep. 30, 1992, published as WO93/07468, Apr. 15, 1992, now U.S. Pat. No. 5,471,311.

TECHNICAL FIELD

This invention relates to systems for revealing information about a material by controlled illumination of the material and the monitoring of diffused or scattered transmitted light from the material. The material may be comprised of a solid object or objects. The invention also relates to establishing information about the properties of, for example, a fluid or flowable material. In particular, however, the invention is based on scanning an object with a point light source and comparing directly reflected light levels with diffused or scattered transmitted light levels.

The invention has a multiplicity of applications. A particular application relates to the detection of defects on individual fruit or vegetable products such as tomatoes for separation out or rejection, and/or to grading the ripeness of such products. A further application of the invention is directed to a sorter for separating extraneous matter from vegetables such as potatoes, in particular at high capacities in excess of 50 tons per hour. The invention may thus be employed in general in the detection of characteristics of organic or living material. The invention may also be applied to the provision of information about the characteristics of inorganic but light-transmitting substances.

BACKGROUND ART

Numerous systems are known for, in particular, classifying articles by optical characteristics, such as their color. In U.S. Pat. No. 2,678,725, a classification system is described in which two light beams of different colors are directed at articles to be classified. The system is arranged to provide dual outputs, one of which is related to the chromaticity of the articles, this being defined as their redness or blueness, and the second output being related to the brightness of the article, namely its lightness or darkness.

According to U.S. Pat. No. 3,675,769, a mixture of potatoes and stones and soil is conducted beneath a source of visible and invisible light. A detection system responsive to the light reflected by the mixture of materials classifies the material monitored into two categories based upon the ratio of their reflectivities within selected radiant energy bands. Associated sorting means directs useful product into an appropriate collection feature while discarding the unwanted stones and soil.

U.S. Pat. No. 3,776,381 provides a method for sorting products in which light reflected from product is monitored by light-sensitive cells to detect products that are too light, too dark or otherwise defective. U.S. Pat. No. 3,910,701 provides a method and apparatus for measuring light reflectance, absorption and/or transmission, in which light of different wavelengths is directed towards a test piece, and reflected and/or transmitted light from the test piece is monitored by a light-responsive sensor. U.S. Pat. No. 3,939,983 relates to apparatus for grading and sorting tobacco, in which tobacco leaves are scanned by detectors monitoring the reflectivity of the leaves. Outputs from the detector control an ejection system for separating those leaves having the required reflectivity characteristics from those leaves which are to be discarded. U.S. Pat. No. 4,081,362 is directed to specific mechanical aspects of a fruit sorter, in which a color sorting system is applied.

In U.S. Pat. No. 4,095,696, a tomato monitoring system making use of three photodetectors, each having a different spectral response, is described. Each detector monitors a different wavelength of light reflected from the tomato. Logic circuitry operating on the outputs of the three detectors enable red tomatoes to be separated from all other articles on the conveyor, including dirt and rocks. U.S. Pat. No. 4,120,402 describes a further product sorter suitable for separating green tomatoes from red tomatoes and also for the removal of foreign objects such as dirt and debris from a flow of tomatoes to be sorted. This system uses two pairs of phototransducers, each having a respective specific color filter.

U.S. Pat. No. 4,134,498 discloses a further sorting system in which light reflected from articles of two predetermined wavelengths is monitored and processed to provide a classification signal functionally related to the ratio of the respective signals at the different wavelengths. A further system using two different wavelengths of light is described in U.S. Pat. No. 4,146,135, in this case directed to the detection of peach pits and peach pit fragments remaining in peach halves following a pitting operation.

Yet another system employing radiant energy at bands of two mutually different wavelengths is disclosed in U.S. Pat. No. 4,186,836. Downstream signal processing in conjunction with removal devices enables the required sorting action to be achieved.

U.S. Pat. No. 4,204,950 describes a produce grading system in which reflected light from an object is monitored in four color bands, two in the visible range and two in the invisible range. Comparison of color combinations enables the system to detect the presence of a desired color or an undesired color, and also to determine the characteristics of the product, namely whether it is vegetable or non-vegetable matter. In U.S. Pat. No. 4,281,933, fruit sorting apparatus is described in which the color of the fruit is detected by directing light signals onto opposite sides of the fruit and processing electronic signals derived from the reflected light levels to produce the required information to enable suitable sorting action to be effected.

German Published Patent Specification No. 2,319,721 describes a further optical sorting system while yet another such arrangement is disclosed in Japanese Patent Specification No. 54-144662.

One or more of a variety of problems or deficiencies may be identified in many known systems, such as those adverted to above, although not all of the problems subsequently indicated are necessarily experienced in every such system. Nonetheless, many optical sorting systems are distinguished by substantially total dependence on directly reflected light from the product surface to provide information for the sorting process. Many such systems are also limited to typically one or two spectral bands of illumination, and even where more than two such bands are employed, the dependence on reflected light remains. A very particular deficiency of many existing systems is an inability to detect or analyse small features. Furthermore, the majority of existing or known systems are unable to identify defects. Even in systems capable of identifying the presence of defects, classification of any particular defect as to its nature is not generally available. The detection of different surface textures and the identification of surface imperfections of a variety of different kinds are also features not in general available in known systems. A further specific limitation is the inability of the majority of existing optical sorting systems to operate on anything other than a limited area of the product. Thus defects outside the field of monitoring or observation of the system may go undetected. A related deficiency or problem is a reduced level of inspection sensitivity away from the central region of the product lying directly under the monitoring light source.

It is an object of the invention to provide an information gathering system overcoming at least one of the foregoing deficiencies or problems. It is a specific object of the invention to provide a product sorting system in which one or more of the foregoing problems or deficiencies are addressed.

DISCLOSURE OF INVENTION

According to the invention, there is provided an information gathering system comprising:

(a) means for directing a light beam at material for which information is required in respect of at least one specified characteristic or property, to impinge upon a target region of said material, (b) means for detecting light emanating from a region of said material other than said target region, said region other than said target region being substantially adjacent to or contiguous with said target region, and (c) means for deriving, from said emanating light detecting means, a signal indicative of said at least one specified characteristic or property of the material.

The information gathering system according to to the invention preferably further comprises means for detecting reflected light returned from said target region, said signal deriving means being adapted to provide a signal indicative of a specified characteristic or property of the material by comparison of the relative levels of said emanating light and said reflected light.

In a favored embodiment of an information gathering system according to to the invention, at least said reflected light detecting means may be located substantially in proximity to said light beam directing means. Preferably, said emanating light detecting means is also located substantially in proximity to said light beam directing means. Thus either or both light detecting means of the system of the invention may suitably be aligned substantially in the direction of the light beam. Alternatively however, said light detecting means may be located along an axis or alignment not substantially coincident with that of the light beam. Means such as mirrors may enable said light detecting means to be responsive to light signals issuing initially substantially in the direction of or parallel to the light beam.

According to a further favored aspect of the information gathering system according to the invention, means are provided for effecting scanning displacement of said light beam relative to said material. Suitably, said scanning displacement of said light beam is effected mechanically.

Said light beam directing means preferably comprises at least one light source, and said at least one light source may be a laser. Alternatively, said light beam directing means may comprise a plurality of light-emitting diodes.

Said means for detecting reflected light preferably comprises a sensor portion responsive to light to generate an output signal. Said means for detecting emanating light suitably also comprises at least one sensor portion responsive to light to generate an output signal. In a favored arrangement, a single sensor portion is provided for detecting reflected light and two sensor portions for detecting emanating light. Preferably, said sensor portions comprise a plurality of light-responsive strips, and each of said light-responsive strips may provide an output signal indicative of the magnitude of the light input at any location along the length of the strip, without identification of the location of said light input.

Alternatively, said sensor portions may comprise a plurality of photo-detectors.

In any embodiment an information gathering system according to the invention, optical means are suitably provided for imaging light received from said material for which information is required.

In a still further variant of an information gathering system according to the invention, said light beam directing means may be a scanning laser and said light detecting means may comprise a light-responsive sensor, said scanning laser and said sensor being synchronised for correlation of the laser scan pattern with an instantaneous reception region of said sensor.

The invention also encompasses a system for establishing properties of vegetable or other comestible products, comprising an information gathering system according to the foregoing aspect of the invention. A system of this kind may comprises a reject mechanism and data processing and analysis features for providing output signals to said reject mechanism. The system provided according to this aspect of the invention may also comprise at least one non-optical monitoring means for providing information in respect of at least one specified characteristic or property of the material.

BRIEF DESCRIPTION OF THE DRAWINGS

The invention will now be described in more detail having regard to the accompanying drawings, in which.

DESCRIPTION OF THE PREFERRED EMBODIMENT

Figure 1:
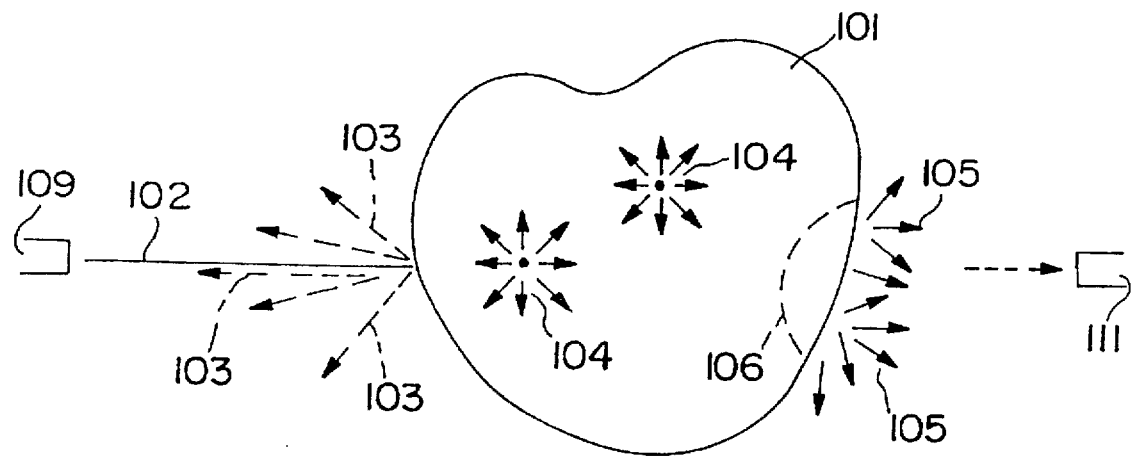
FIGS. 1 and 2 are diagrammatic illustrations of the light diffusion or scattering process in a product, which creates the illumination or light emanation effect on which the invention is based.
Figure 2:
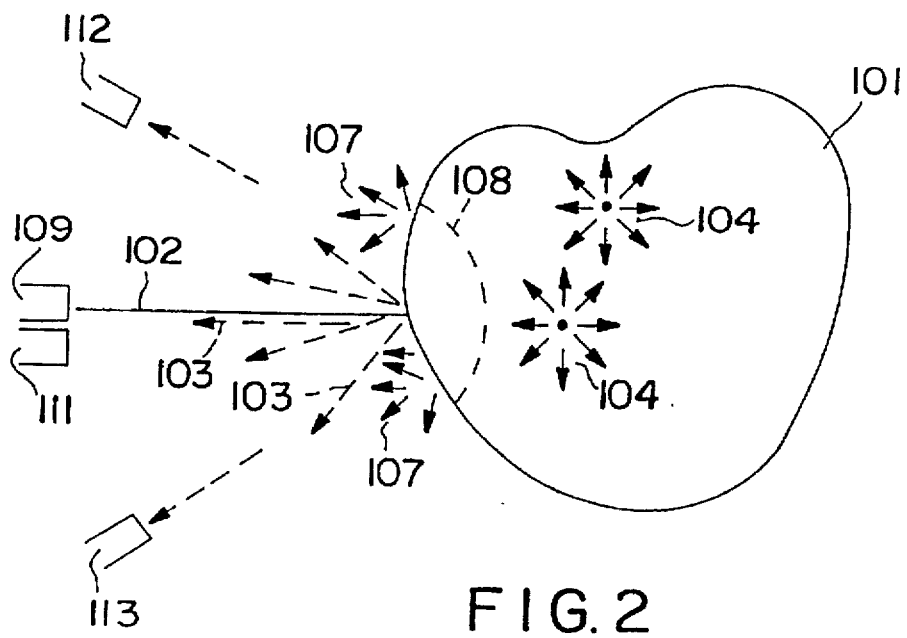

FIGS. 1 and 2 show the light diffusion or scattering process in a product or object 101, such as a tomato, which creates the product illumination and light emanation effects on which the invention is based. As shown in FIG. 1, a light beam 102 is directed onto the surface of object 101. Direct reflection of light from the surface of object 101, in particular in the direction of the light source 109, is indicated by reference 103. Depending on the nature of the surface of the object, a greater or lesser proportion of the initially incident light will be reflected. In an organic material, such as a tomato, the remainder of the light will pass into the cellular structure of the product and is subjected to a scattering process, resulting in light becoming diffused throughout the interior of the product and the entire object being, as it were, appearing to be lit up from within, in the manner of an electric light bulb. The scattering process is indicated by references 104. Light reaching a particle or cell of the structure of the object is scattered by the cell or particle and transmitted to further cells or particles, where the scattering process is repeated.

It is known to monitor the level of this scattered or diffused light emanating from a surface area of the product opposite to the point of incidence of the light beam. Such emanating light is indicated by reference 105 in FIG. 1 and a notional boundary of an emanating light region to be monitored by a sensor 111 is designated by reference 106. Effectively this emanating light 105 is light which has been transferred or transmitted through the product from the point of incidence of light beam 102. A deficiency of this known method of deriving product information by monitoring through-the-product light output is that the signal magnitude is affected by the size of the product. Furthermore, the level of light on the opposite side of the product from the light beam is in any case significantly attenuated and affected by the light transmission properties of the product. The technique is not suited to providing information about product defects and in particular information about surface imperfections or abnormalities.

The principle underlying the present invention is illustrated in FIG. 2, in which emanating light returned by the object 101 on the side of the object directed towards the light source 109 is monitored. The boundary of a region of the object surrounding the point of impact or target region for the light beam 102 is designated by reference 108. The returning emanating light 107 in this so-called "halo" region 108 surrounding the target region for the light beam 102 may be monitored or detected by a sensor assembly or system 111 substantially aligned with the light beam 102, so that the sensor may be located substantially alongside or in proximity to or in the vicinity of the light source 109. No such constraint is however essential in the application of the invention and the monitoring or detecting of the emanating returned light 107 may alternatively be effected by a sensor located to the same side of the object as the light source 109 but along a direction which is not aligned with the light beam 102, such as sensor 112 or sensor 113. Thus the direction of sensing may be angularly displaced relative to the direction of the light beam 102. The sensor may also be arranged to be responsive to light signals initially parallel to the light beam, even if itself disposed elsewhere, by suitable deflecting means, such as a mirror or mirrors.

Preferably, the invention combines detection of both directly reflected light 103 returned form the surface of the object with simultaneous detection of the diffused or scattered light emanating from the object within the halo region 108, and comparison of the relative levels of these light signals enables significant useful information to be derived. Particular advantages of monitoring the emanating returned light 107 are the significantly higher intensity of the returned light signal as compared with the levels of light 105 emanating from the opposite side of the product, as well as the possibility of deriving additional information concerning both the surface region of the tomato and also subsurface condition, especially as affected by defects occurring relatively close to the surface of the product. In particular, the output of emanating returned light 107 is substantially unaffected by product size.

The so-called halo created by light diffusion or scattering within the product 101 and monitored within the boundary region 108 by a sensor or sensors 111, or 112 and/or 113, in a system according to the invention, does not, it will be appreciated, have a definitive boundary. In the case of tomatoes, for example, the interior of the product is substantially lit up by the application of incident light beam 102, and the intensity of this interior illumination decreases with radially outward distance along the surface of the tomato from the point of incidence or target region of the light beam 102. Thus the halo effect is substantially continuous, but of diminishing intensity, and boundary 108 is intended to represent merely an effective limit of the region within which the emanating returned light 107 may be monitored, and does not indicate any termination of the interior illumination of the object resulting from light diffusion and scattering.

Figure 3A:
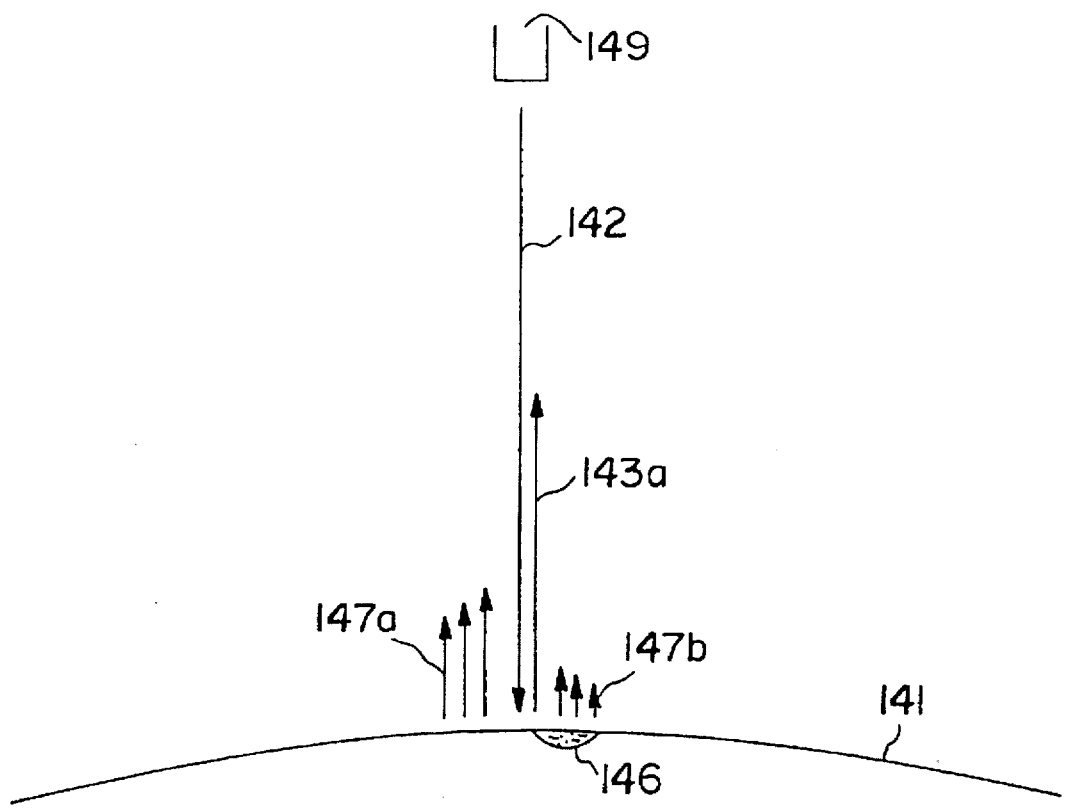
FIGS. 3A and 3B show diagrammatic representations of light signals returned in the direction of a light source from a surface exhibiting abnormalities, for different points of incidence of a light beam.
Figure 3B:
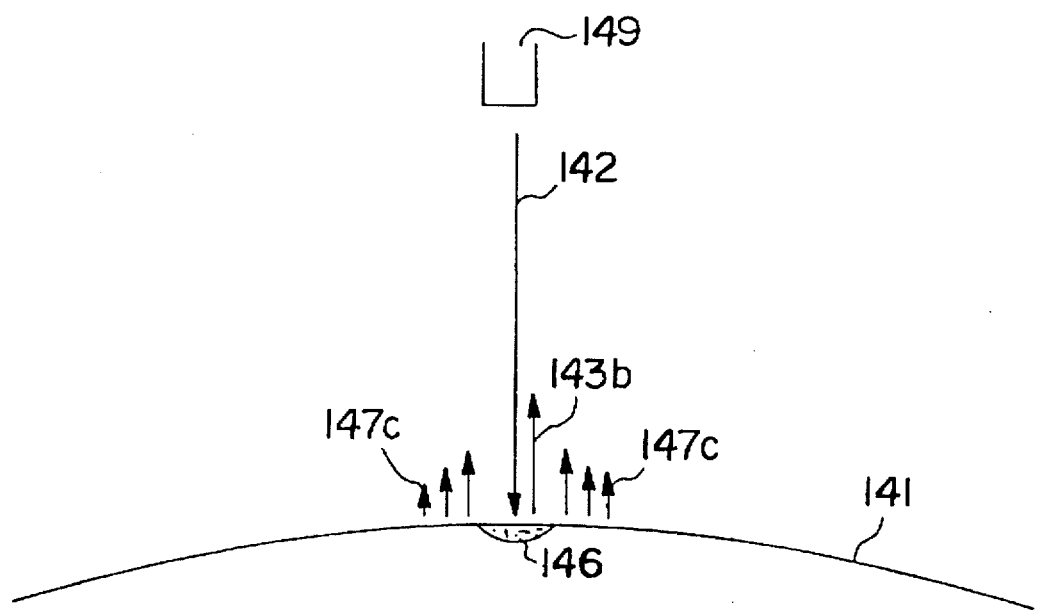

This light dispersing or scattering property of an organic product may be employed to assist in the detection of defects in, for example, a vegetable product such as a tomato in the manner illustrated in FIGS. 3A and 3B. In FIG. 3A, a light beam 142 is incident on a normal area of the surface of a product 141, with a defective area 146 being located to the right of the instantaneous point of incidence of the light beam. There is thus a normal or expected level of direct reflection 143a back substantially in the direction of or parallel to the line of incidence of the light beam 142, and also a normal level of returned light 147a from the region to the left of the point of incidence or target region of light beam 142. To the right of the point of incidence of the light beam 142 however, a very much lower level of emanating light 147b is returned from the defect area 146, thereby enabling the presence of a defect to be noted and monitored. Increased absorption of light by the defect material reduces the level of light returned. The relative sizes of the arrows designating these reflected light and emanating light signals are intended to provide a quantitative indication of the relative strengths of these light signals in the direction of the light beam, as perceived by a sensor arrangement located in proximity to the light source 149.

In FIG. 3B, the light beam 142 is now shown as incident on the actual defective area 146 itself. In this case, there is not only a reduced or abnormally low level of direct reflection 143b from the defect area, back along the line of or parallel to the incident beam, but there is also a reduced level of internally scattered or dispersed light 147c returned from the entire halo region surrounding the target region of beam 142, by virtue of the abnormal scatter pattern engendered by the presence of the defect 146 at the point of impact of the light beam. Thus it will be seen that by traversing a light beam along a path across the surface of a tomato for example, significant information may be derived relating to surface and sub-surface properties of the tomato by observing the changes with beam position in the levels of directly reflected and returned emanating light. Not only is the presence of a defect indicated by changes in the levels of the reflected light and returned emanating scattered light or dispersed light signals individually, but also additional information in respect of the defect may be derived from the variation in the levels of these light outputs and in their relativity according as the light beam is moved over the surface of the material forming the product under inspection.

Figure 4:
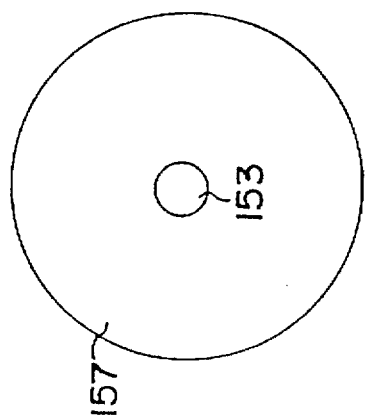
FIG. 4 is a diagrammatic representation of the manner of imaging light signals, such as those of the kind described in respect of FIGS. 4A and 4B, returned from a material to be examined in accordance with the principles of the invention.
Figure 4:
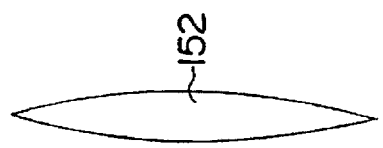
Figure 4:
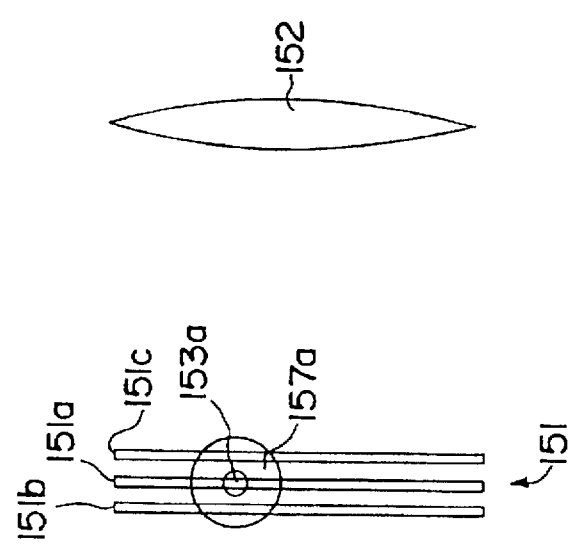

This principle may be adopted in a practical sensor or detector assembly by imaging a directly reflected light spot 153 onto a photosensitive sensor assembly 151, as shown in FIG. 4. In addition to imaging this direct reflection signal 153 onto the sensor 151, the glow of the transmitted and scattered light emanating from the halo region 157 surrounding the point of incidence of the light beam is also imaged onto the sensor 151. By arranging three line detectors 151a, b and c side by side and imaging the direct reflection onto the centre detector, such as by the lens 152 of FIG. 4, the two side detectors 151b and c adjacent to the central detector 151a monitor the light levels returned from the halo region 157, namely emanating scattered or dispersed returned light levels. The imaged regions on sensor assembly 151 corresponding to spot 153 and halo 157 are designated in FIG. 4 by references 153a and 157a respectively, in the image plane at the sensor. Image spot 153a may be wider than central detector 151a, but must not be so wide as to impinge on side detectors 151b and c.

In a practical application of this principle, a light beam may be scanned across a conveyor carrying product, the scanning direction being substantially transverse or at right angles to the direction of product advance, and the image of the scanned beam may be picked up by a photoreceptive sensor comprising three photosensitive line detectors aligned along the scanning direction. Such an arrangement of detectors ensures that the light beam from a scanning laser, for example, is always imaged onto some point of the line detectors of the sensor assembly. An embodiment of this kind will be subsequently described in fuller detail. In brief, however, an output signal from each of the three photosensitive detectors may be converted from a current signal into a voltage signal and then amplified. The amplified signals may then be further processed to firstly detect whether a product is present, and then whether the product is abnormal by virtue of its light-transmitting and/or absorbing characteristics. Associated memory means is provided to enable the system to remember the size and shape of the object in the event of a product being present, to count any defects present, and also to monitor intensity differences possibly indicative of flaws in the object due to skin breakages, mold, and stem or blossom end, and to differentiate between acceptable defects and defects which require product to be rejected.

Figure 5:
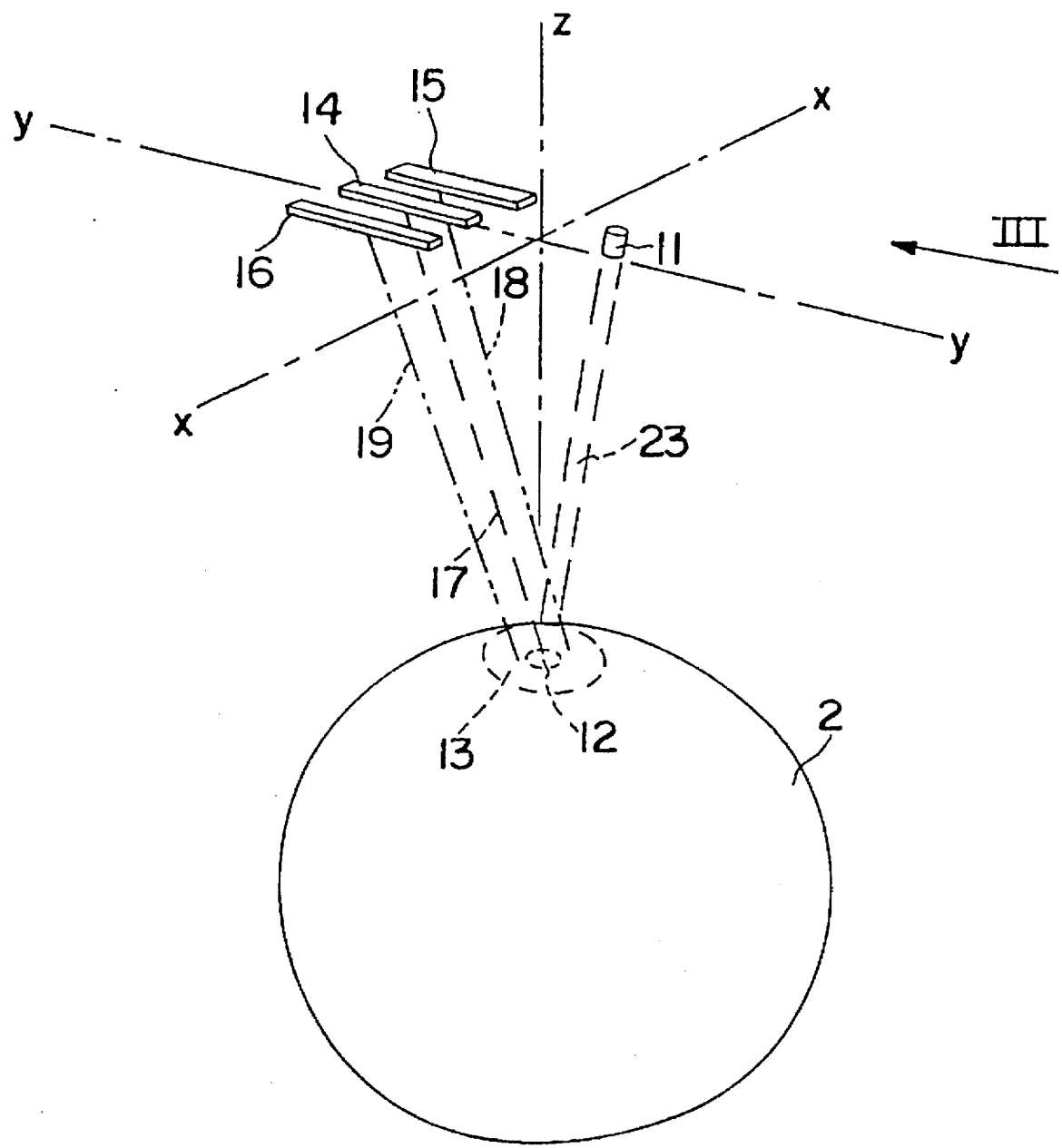
FIG. 5 is a diagrammatic pictorial representation of the manner of application of the principles of the present invention.

FIG. 5 is a further pictorial representation of the principles of the invention as applied to a method of inspection of a fruit or vegetable product. A light source 11 directs a beam 23 of light onto the surface of a product 2. The spot of light where beam 23 impinges on the surface of product 2 is designated by reference 12. In the case of a product which is substantially transparent or translucent to light, so that light impinging on a surface portion of the product can pass to at least some extent through the substance or the material of the product, a diffused light region 13 will become apparent round the target spot or point of impingement of light beam 23 by virtue of scattering or dispersal of light within the material of the product. In the case of a tomato or similar product, the application of a concentrated light beam to the surface of the product can result in the entire product becoming lit up, so that a succession of diffused or scattered light regions 13 may be defined, extending concentrically outward from target spot 12, each successively more outward diffused light region being illuminated to a lesser degree of intensity.

In the detection system of the invention as depicted in FIG. 5, preferably three detectors are used, a central detector designated by reference 14, a rear detector indicated by reference 15 and a front detector 16. Central detector 14 is arranged to be responsive to directly reflected light returning along the path designated by reference 17 from the target point or impingement spot 12 of light beam 23 on the top surface of product 2. Rear detector 15 is arranged to be responsive to or "see" diffused or scattered light emanating from a portion of the region 13 which is radially outward from and surrounds the central or target spot 12 as shown in FIG. 5. Front detector 16 is similarly responsive to diffused light emanating from another portion of the diffused light region 13. References 18 and 19 respectively indicate notional paths for light returned from or emanating from region 13 for perception by detectors 15 and 16.

In the case of an inspection system of the type already discussed, a path of advance for the product to be monitored may be designated by the axis identified as "x—x" in the representation of FIG. 5. The axis identified as "y—y" the designates a dimension or the direction extending across the width of the belt or other conveyor feature of the system on which the product is advanced, in other words, the transverse dimension of the system relative to the direction of product travel. The z-axis is thus a vertical axis extending upwardly broadly perpendicularly to the x-y plane. In an arrangement of the invention especially applicable to the sorting of fruit and vegetable products, the light source 11 and the central detector 14 are suitably disposed in the y-z plane, i.e. a plane which is substantially normal or at right angles to the direction of advance of the products at the time of inspection. The x—x direction indicates the path of travel of the product at the moment of inspection. This path of travel may be on a surface defined by, for example, a belt, or on a plane substantially defined by the uppermost peripheral portions of a series of rollers, prior to reaching an inspection zone. The path of travel may remain, at the actual inspection zone, substantially the same as during the advance phase, or alternatively, the path of travel during product inspection may be a portion of a freefall trajectory at the moment of actual inspection and/or a direction tangent to a belt surface at its end region where it curves around a support or drive roller at the point of throw-off of the advancing product. Irrespective of the actual orientation of the x—x direction, the three axes, x, y and z, are suitably mutually orthogonal. The y—y axis then defines a direction of scanning for displacement of the light beam across the surface of the material to be monitored to thereby provide for inspection or monitoring of a band or zone across the product.

Figure 6:
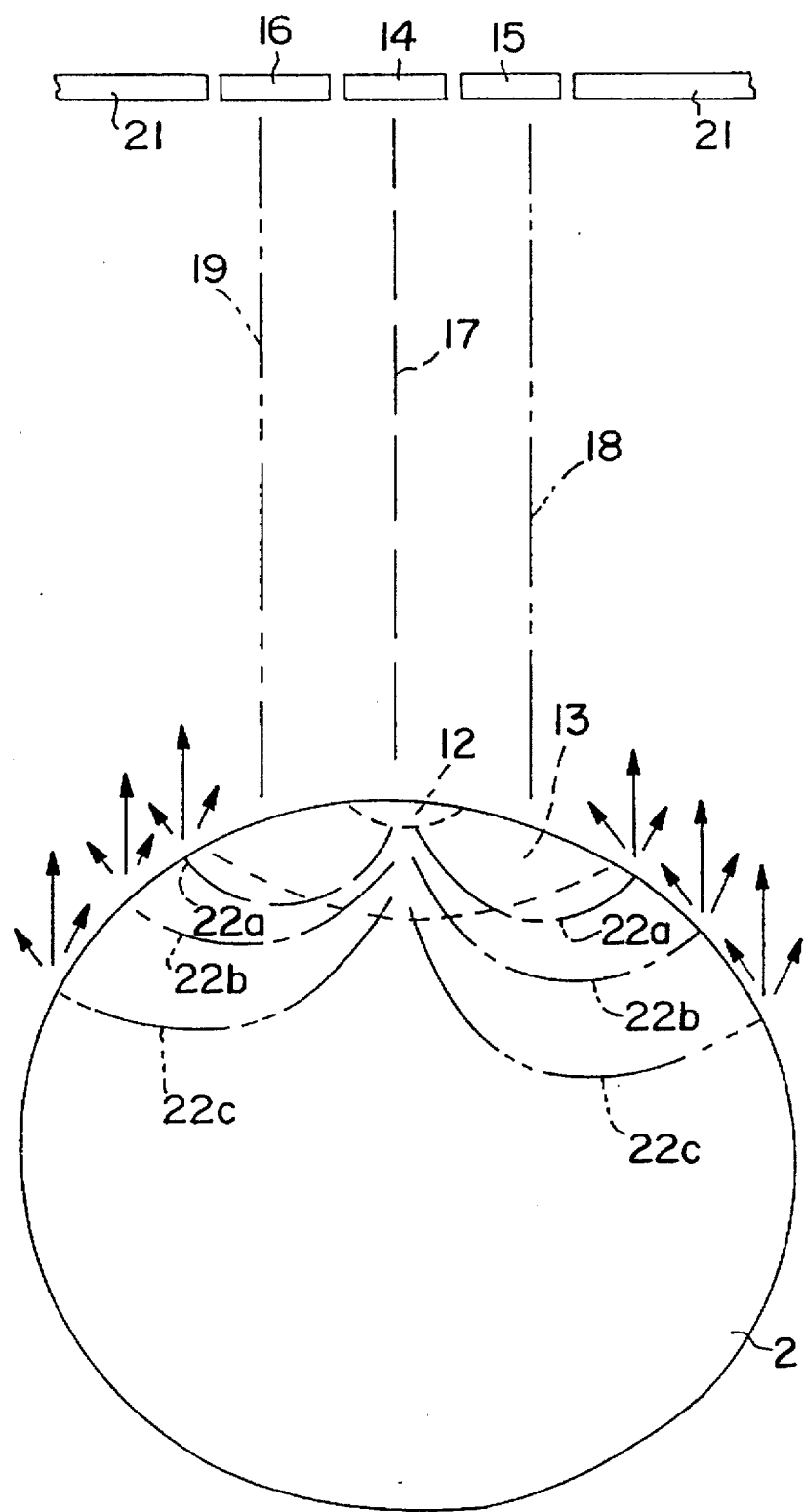
FIG. 6 is a diagrammatic side view further illustrating certain aspects of the technique of the invention as depicted in FIG. 5.

FIG. 6 is a side view showing certain of the features of the arrangement of FIG. 5 in the direction of the arrow III of FIG. 5. In addition to references already identified in connection with the description of FIG. 5, FIG. 6 also shows a fragmentary indication of a support structure 21 for the detectors 14, 15 and 16, as well as an indication of notional possible paths of travel for diffused or scattered or dispersed light, references 22a, 22b and 22c, passing through the product 2 from the target light spot 12 to bring about the emanation of light from various regions on the surface of the product, of which that monitored by detectors 15 and 16 is again designated by reference 13.

Thus, in the case of a tomato, the application of a concentrated light beam results in illumination of the entire surface of the tomato, the intensity of the illumination decreasing with the outward or radial distance or spacing from the point of impingement of the light beam. A similar effect takes place in other like products. The effect is not however necessarily restricted to fruit and vegetable products and may also be identified in and applied to living organic material and to inorganic substances having light transmitting and/or diffusing or scattering properties.

Figure 7:
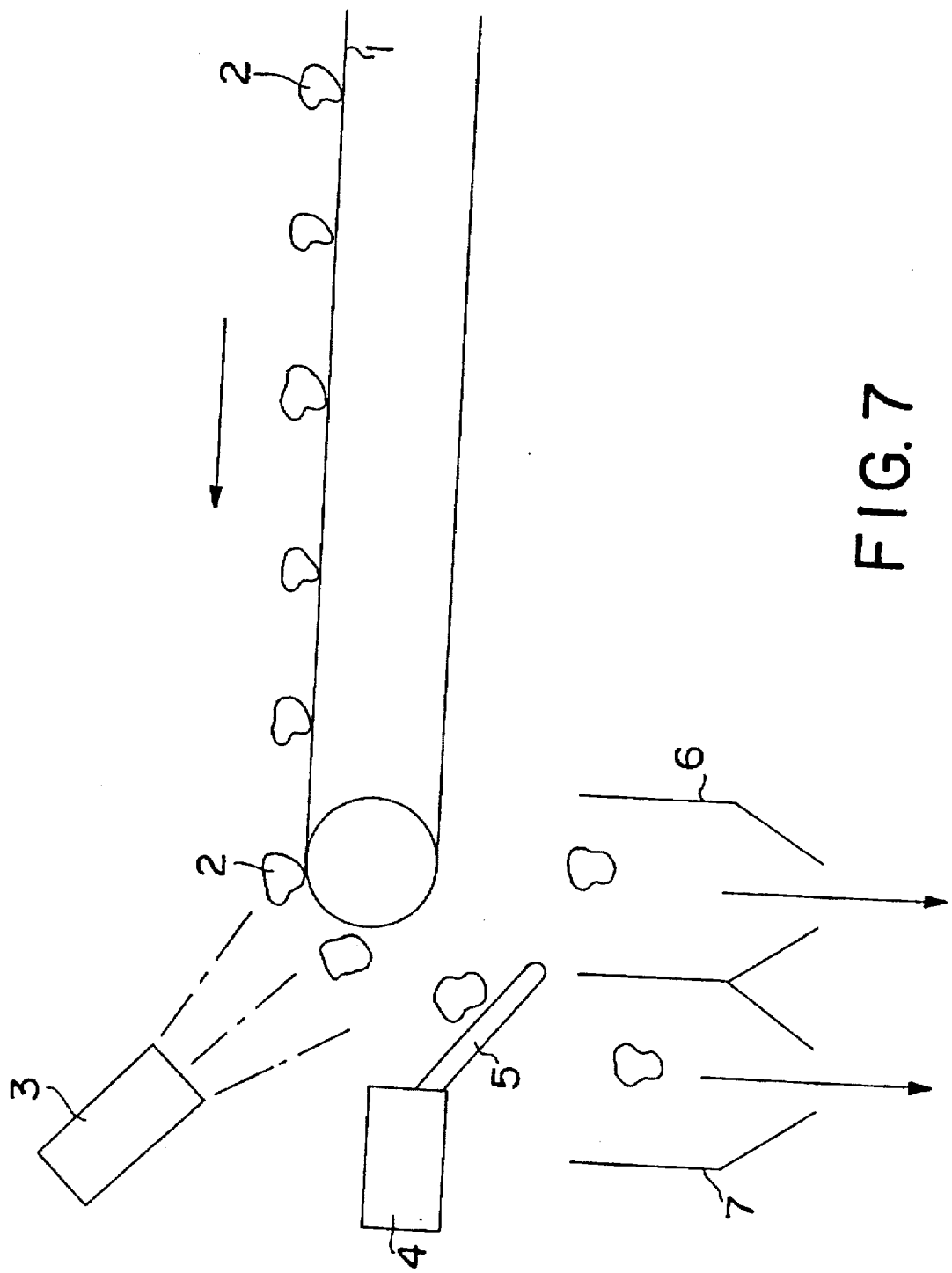
FIG. 7 is a schematic side view of a sorting device embodying the principles of the invention.

An embodiment of fruit or vegetable sorting apparatus embodying the features of the invention will now be described as a whole, having regard to FIG. 7. As shown in FIG. 7, a flat belt conveyor 1 advances product 2 to be monitored and inspected to an inspection station. At the inspection station, an electronic inspection device 3 is mounted above and at the end of the flat belt conveyor 1. Also mounted at the same end of the conveyor but below the level of the belt 1 is a reject mechanism 4. Both the inspection device 3 and the reject mechanism 4 are substantially the same width as the belt. Both the inspection device 3 and the reject mechanism 4 thus extend transversely across the entire path of advance of product 2 on belt 1, so that all product conveyed forwards by the belt may be monitored, inspected, and accepted or rejected as appropriate.

Product 2 dropping off the end of the belt 1 falls onto a sloping surface defined by movable fingers 5 which define the operating elements of the reject mechanism 4. During the freefall period after the product leaves the conveyor but before it reaches the fingers, the falling product 2 is inspected by the monitoring features of the inspection device 1. In a modified adaptation of the system schematically shown in the drawing, on-conveyor inspection may take place instead of free-fall monitoring, and product advance may take place on a conveyor provided with rollers, rather than the flat belt shown. If a particular individual product is defective or a particular item inspected is to be rejected, a signal is sent from device 3 to the rejector 4 which opens the relevant fingers 5 to allow the defective product or extraneous material to be removed from the product stream by falling into a discharge arrangement. Reference 6 denotes a bin or reception arrangement for good product for further advance, into which good product 2 is deflected by the angled or sloping fingers 5 in their normal or raised operating disposition. Reference 7 denotes a bin or path of advance for reject product, into which defective product falls by virtue of fingers 5 being rotated downwardly and to the left as shown in FIG. 7, in which disposition they fulfill no deflecting function and the defective product or extraneous matter continues its freefall path of movement into bin or receptor 7. The inspection device of the invention may be adapted to detect defective product and/or the presence of extraneous matter. In the case of fruit or vegetable products, defective product may include unripe or overripe product, while extraneous matter may include earth, leaves and other unwanted vegetable material.

Figure 8:
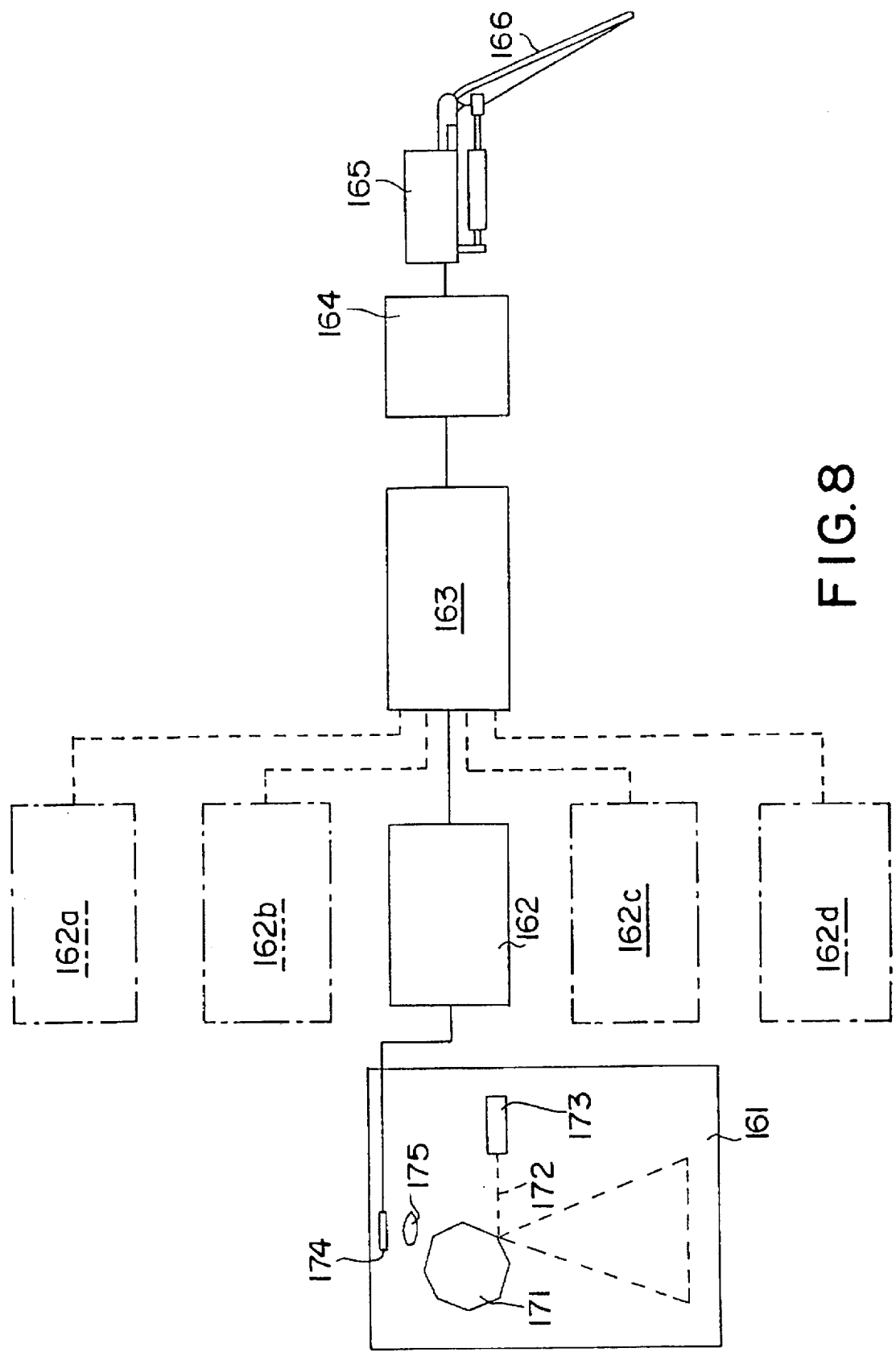
FIG. 8 is a block diagram showing the manner of carrying out sorting operations in a device in accordance with FIG. 7, FIGS. 9A and 9B are a diagrammatic representation of scanning action as embodied in a preferred construction of system according to the invention.

FIG. 8 is a block diagram of a sorter system such as is shown in mechanical schematic representation in FIG. 7. Moving from left to right in the block diagram, the sorter comprises the following five sections: scanner and detector or sensor assembly 161, signal processing 162, image analysis 163, rejector logic 164, and rejector mechanism 165. The features such as shown in FIGS. 7 and 8 essentially comprise a subsystem of a complete sorter facility, which will suitably further include a roller or other conveyor, a wiper system, a clean-in-place system and a control feature, preferably including a control panel or other control arrangement.

In the system of FIG. 8, the scanner suitably consists of a rotating multi-faceted mirror 171, which reflects a laser beam 172 from a laser 173 in a scanning motion down onto product passing beneath the scanner unit on a conveyor, as distinct from the free-fall inspection of FIG. 7. The rotation of the mirror 171 is precisely controlled and regulated to avoid errors in scanning and thereby any possible position errors in the image of the objects being scanned. Image information is sensed by a sensor assembly 174 from returned light focussed by lens 175, the light signals detected including both directly reflected light from the surface of the product scanned and returning emanating internally scattered or dispersed light from the "halo" region surrounding the target region of the light beam.

The signal processing stage 162 amplifies the signals indicative of light levels provided by sensor 174, to provide numeric data derived from the conversion of voltage values. In the image analysis stage 163, the digital image of the object being scanned is then analysed for information about the physical attributes revealed by the scanning operation, so that the size, shape and other desired characteristics of the object to be monitored may be derived and used for operational decisions based on this information. In this manner, the system is enabled to detect the presence of characteristics such as mold, scars, and stem and blossom end, and to decide whether a particular product is acceptable or is to be rejected.

Output signals from analysis stage 163 drive reject logic 164 to establish which of the fingers 166 of reject mechanism 165 are required to be opened, and for what period, to provide an opening sufficiently large to allow an identified defective object to pass through and thereby be diverted into a reject region away from the flow of good product.

FIG. 8 also shows in dotted outline a number of additional signal processing logic modules 162a, b, c and d providing optional further inputs to, for example, image analysis stage 163. In this manner, information relating to product quality or characteristics derived from other sensing or monitoring techniques may be associated with the reflected and returned scattered or dispersed light information from detector or sensor 174, to enable the system to establish whether a product should be rejected on a combined criterion involving two or more conditions or product assessments.

Figure 9A:
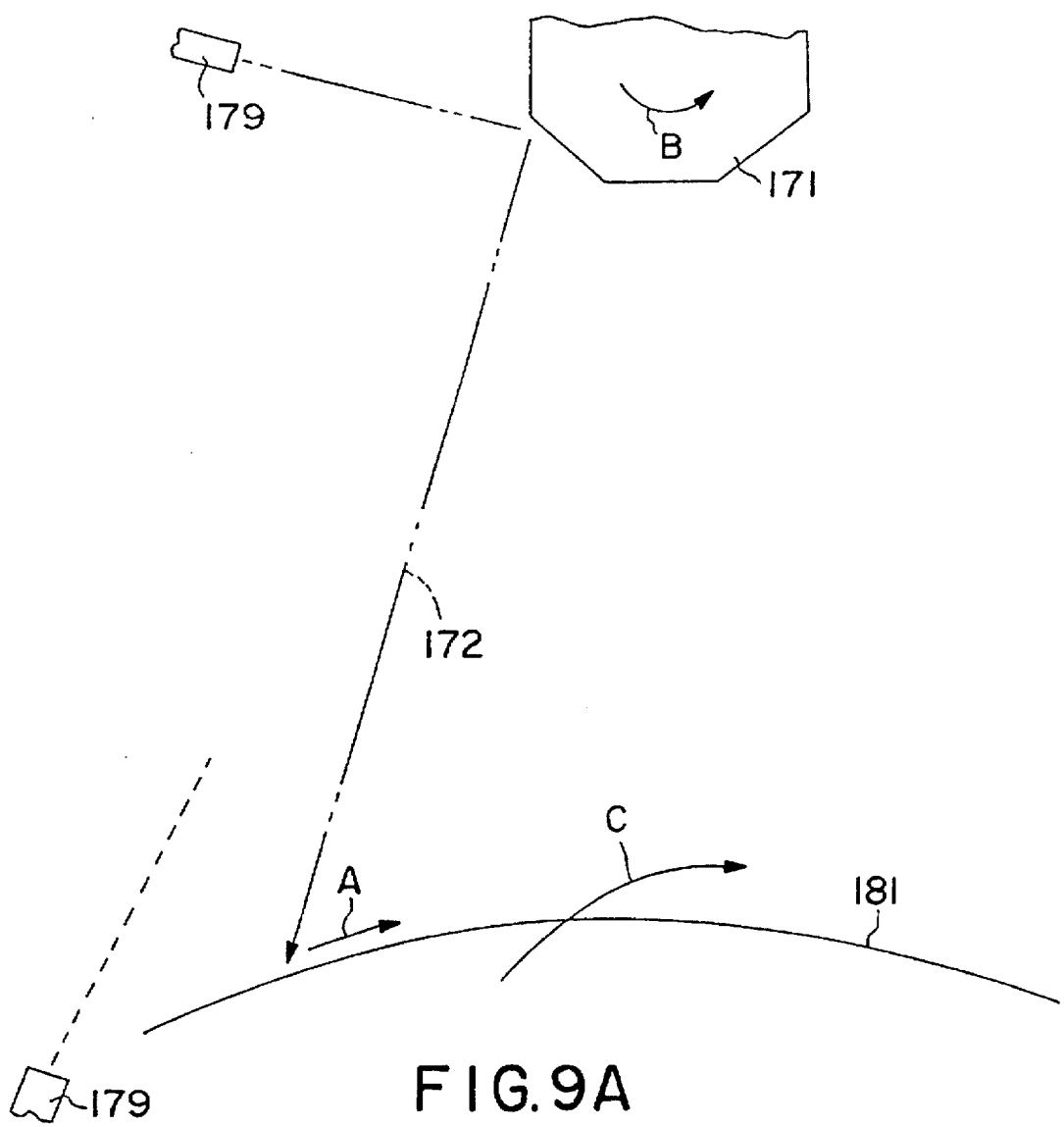
Figure 9B:
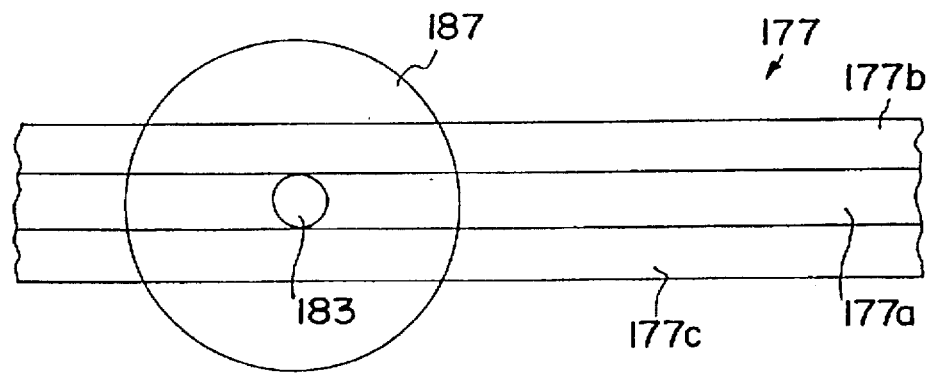

Referring now to FIGS. 9A and 9B, schematic detail of certain features of the laser scanner and detector or sensor assembly 161 of FIG. 8 is shown in FIG. 9A. The light beam 172 is traversed across the surface of a product 181 in a direction (arrow A) substantially at right angles to the path of advance of the product, by using means such as the rotating mirror 171 to achieve the required scanning effect. The laser light 172 used suitably operates at, for example, a wavelength of 670 Nm. On the detection side, imaging takes place along a photosensitive three-part strip 177, FIG. 9B, which is a diagrammatic fragmentary plan view of the strip-form sensor portion 177, showing also the location of the images of the reflected and scattered light. A central strip 177a monitors the direct reflection 183 returned to the sensor assembly 174, while a respective strip 177b, c to each side of the central strip 177a records the level of scattered or diffused light 187 returned. Each light-sensitive strip 177a, b, c is continuous and defines a line detector. There is no incrementation along the length of the strip. Thus any input of light to any location on the strip produces an output signal, but there is no indication per se in the sensor output as to the particular point along the strip which is originating the signal. By use of the scanning feature however, the location in question is determined in the overall system on a time base tied to the scanning rate. Time imaging is determined by the scanning traverse of the spot of light provided by beam 172 across the surface of the object, typically a tomato, and the speed of this traverse is determined by the speed of rotation (arrow B) of the mirror 171 and the angular relationships between the facets of the mirror 171 and other parameters of the system. The start of time imaging is suitably triggered by the point of light initially impacting on a trigger or starting sensor 179, as indicated to the left of the curved product surface 181 in FIG. 9A.

As shown in top view in FIG. 9B, the central strip 177a then reports fundamentally on the directly reflected light, for example, suitably the reflected image 183 of the light beam coming back substantially along the line of incidence of the scanning beam 172. However, in view of the continuous nature of the strip, the signal picked up is not determined solely by the directly reflected light 173 but also by a proportion of the diffused or scattered light 187 emanating from the product in front of and to the rear of the travelling beam of light 172. However, the laterally located strips 177b, c to the side of the central strip 177a detect only returned scattered or diffused light 187 signals.

It will also be seen from FIG. 9A that because of the curvature of the object 181 along the surface scanned, the strength of the light signals returning to the camera will vary as the spot of light travels linearly along the surface, both for the reflected light 183 and for the transmitted or scattered light 187. Allowance may be made for this effect in the signal processing stage.

Successive scans of a globular or generally circular section product may be achieved by rolling or rotating the object 181 during its forward motion, for example, as indicated in FIG. 9A, in the direction designated by arrow C. This aspect of the system of the invention is further identified subsequently.

Thus in summary, each scanning head of the unit, and preferably a number of such heads are provided across the conveyor transverse to the direction of product advance, arranges for an inspecting light beam to be directed onto a rotating multifaced mirror, which in turn reflects the beam down onto product passing under the scanner on a conveyor means in a scanning motion. Light returned from the product flow enables the sorter to make its decisions. The particular parameters of scanner operation, namely size, span, power and speed of mirror rotation, the latter determined in conjunction with speed of product travel, may be varied as required to ensure appropriate operation of the system, while the scanning angle may be changed by increasing the number of facets of the mirror and altering the rotational speed of the mirror. The particular wavelength noted above, namely 670 Nm, is especially suited to tomatoes, in that the response of red tomatoes to this color is notably favorable in terms of the requirements of the invention. Light sources of other wavelengths may however also be used within the scope of the invention, as also may alternative sources of light apart from lasers.

The three line detectors, which may be photo-diodes, serving to detect the reflected and scattered light, are suitably sized to match the other parameters of the system. Amplification and further processing of the detected signals by comparison and digitization steps enable defects or abnormalities to be reported. Such defects or abnormalities are indicated at the line detector features by abrupt attenuation of the returned light signal in particular, namely the scattered light, on account of the incident light not being transmitted through mold or a defect, where present, in the same manner as it would be transmitted through normal tomato material in good condition. Green tomatoes may also be detected with the exemplary system described, in that green tomato is a relatively poor transmitter of the particular light wavelength specified. Analysis of the signal pattern enables differentiation between abnormalities or defects of different kinds, to thereby improve the quality of decision making and to avoid rejection of acceptable product on account of the presence of a condition not justifying rejection.

Figure 10:
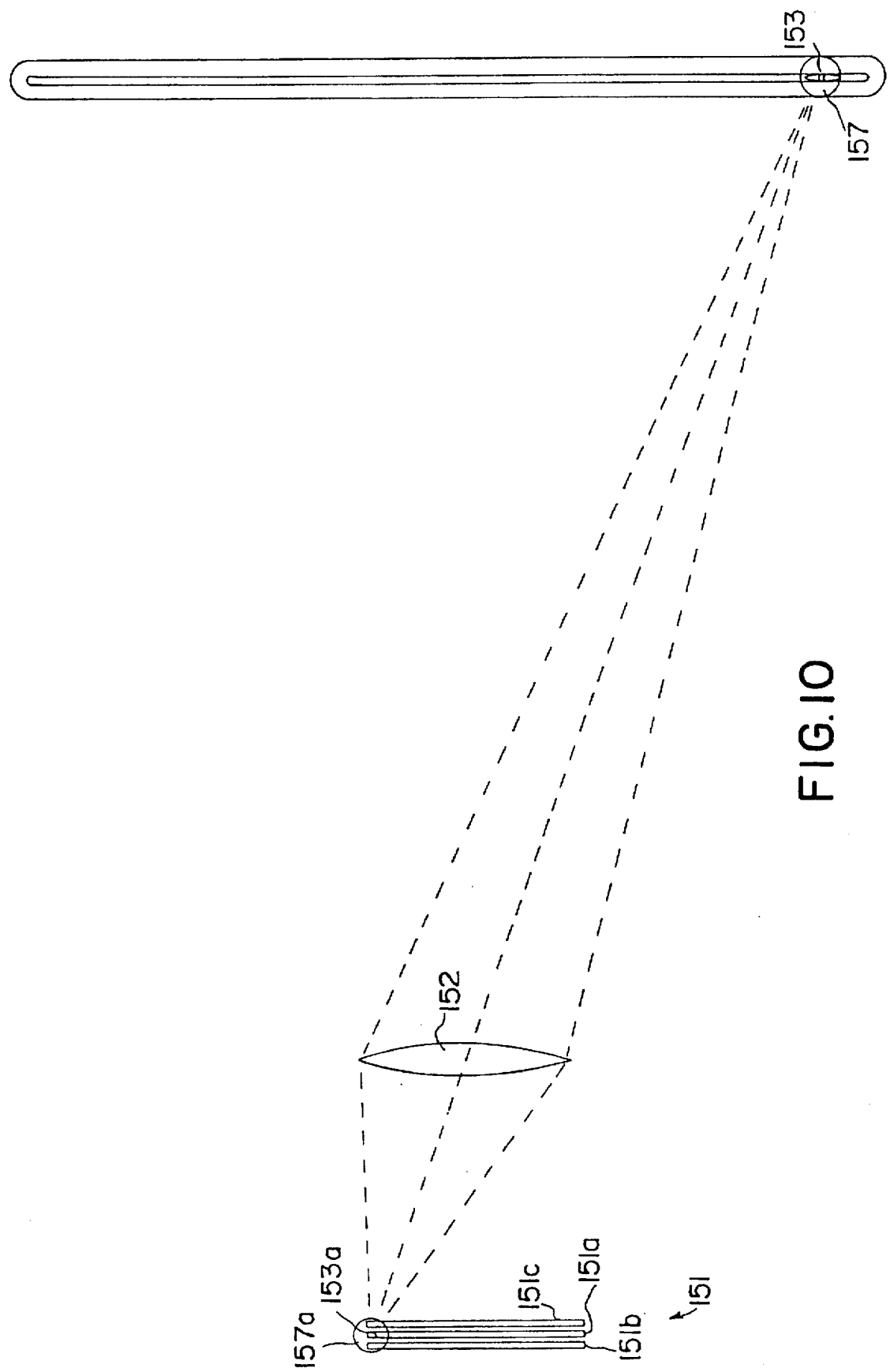
FIG. 10 is a diagrammatic representation of the manner of imaging of reflected light and returned scattered light onto line detectors, in a system embodying the scanning feature of FIGS. 9A and 9B.

FIG. 10 shows further detail of the manner of imaging of light returned from a scan path 159 of, for example, 6 inches length, onto line detectors in a system such as already described in connection in particular with the foregoing FIGS. 9A and 9B. Typically, the lens 152 is arranged to effect a predetermined percentage reduction in image size onto the line detectors. Other reference numerals are the same as those of related FIG. 4.

Figure 11:
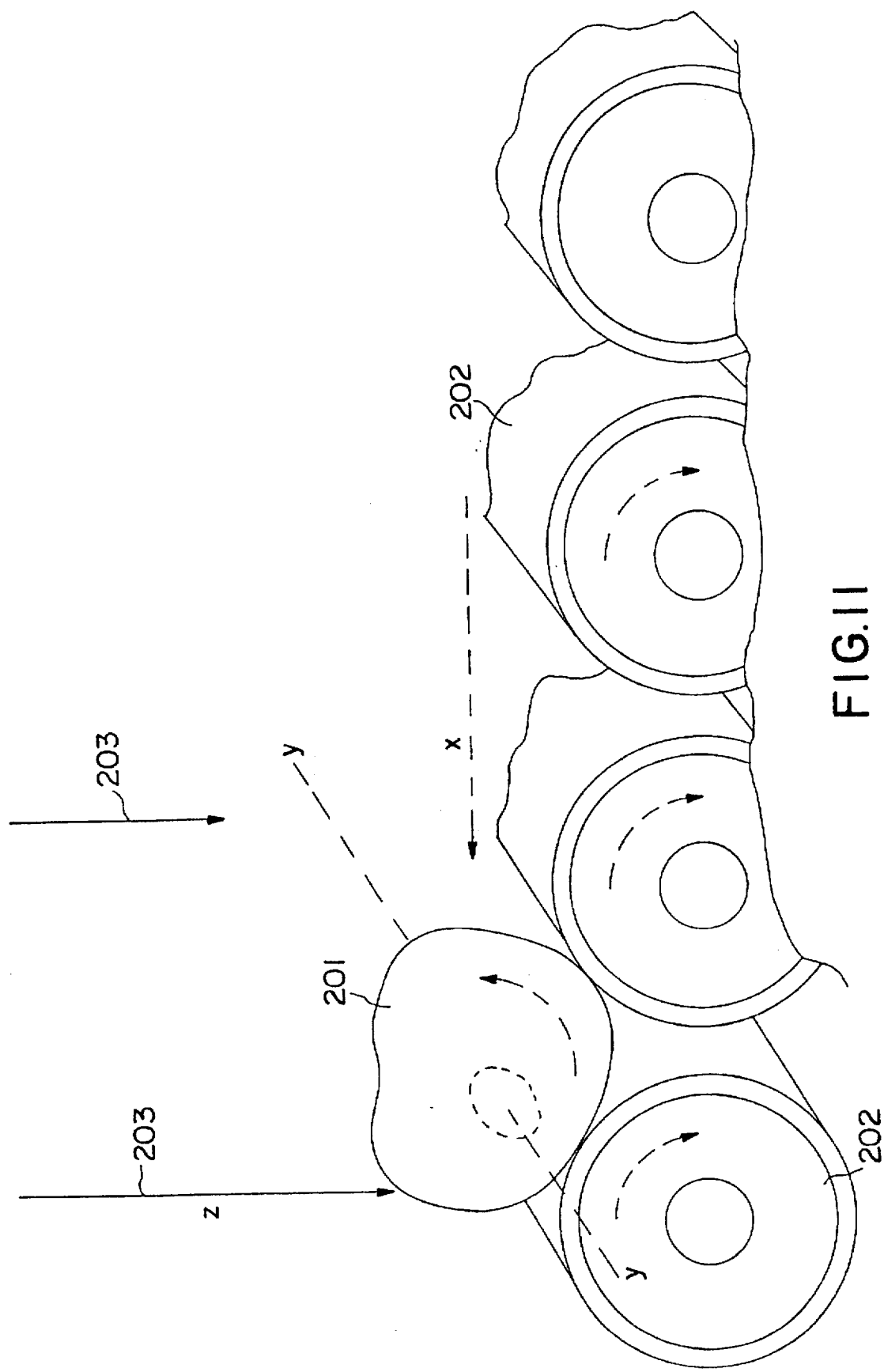
FIG. 11 is a pictorial representation of a manner of object rotation in the scanning zone of a system according to FIGS. 9 and 10.

FIG. 11 shows a particular manner of support and advance of tomatoes in a sorting system embodying the principles of the present invention, directed to providing for substantially full inspection coverage of the entire substantially spherical surface of an advancing tomato 201. The tomato is suitably rolled about a transverse or Y axis as it advances forward in the direction indicated by an X axis in these drawings. The scanning and detection system then suitably operates along a Z axis, for example focussing directly downwardly from above onto the product from a transverse array comprising several scanners and sensors as indicated conceptually by references 203 in FIG. 11. The effect of this manner of product handling is therefore that the product rolls forwardly according as it also travels forwards in the direction of the X axis. The entire periphery of the surface of at least the majority of the tomato is therefore thoroughly inspected during the scanning operation as it rotates about its Y or transverse axis. Enhanced inspection of the regions at the side ends of the product where the Y or rotational axis notionally emerges from the sides of the tomatoes, in other words the area about which the product rolls, is addressed in connection with a subsequent drawing.

The conveyor of the system, which in the particular embodiment under discussion suitably consists of a series of driven rollers 202 on which the tomatoes are supported, thus has two purposes, firstly to transport the product at some predetermined design rate of advance and also to rotate the product through substantially 180° during a predetermined distance of advance of the product through the inspection zone, so that the entire 360° peripheral surface of the tomato in its direction of advance is as it were, "unrolled", while the product remains within the field of view of the monitoring or inspection system. Rotation of the tomatoes represents a particularly economical and effective method of enabling the sorter optics to "see" or monitor all sides or surface areas of the object under examination. It does not however necessarily represent the only method of such inspection and neither is rotation of product to be inspected necessarily a requirement in all product monitoring systems embodying the invention.

In cases where rotation is required, however, selection of appropriate parameters in the system for a suitable nominal size of product enables optimisation of scanning resolution in the context of a particular product and a particular level of production flow. The system of the invention is substantially proof against spurious signals, for example, reflections from roller surfaces, in that the boundaries of an imaged object are monitored and identified and signals from outside these limits may be disregarded.

Figure 12:
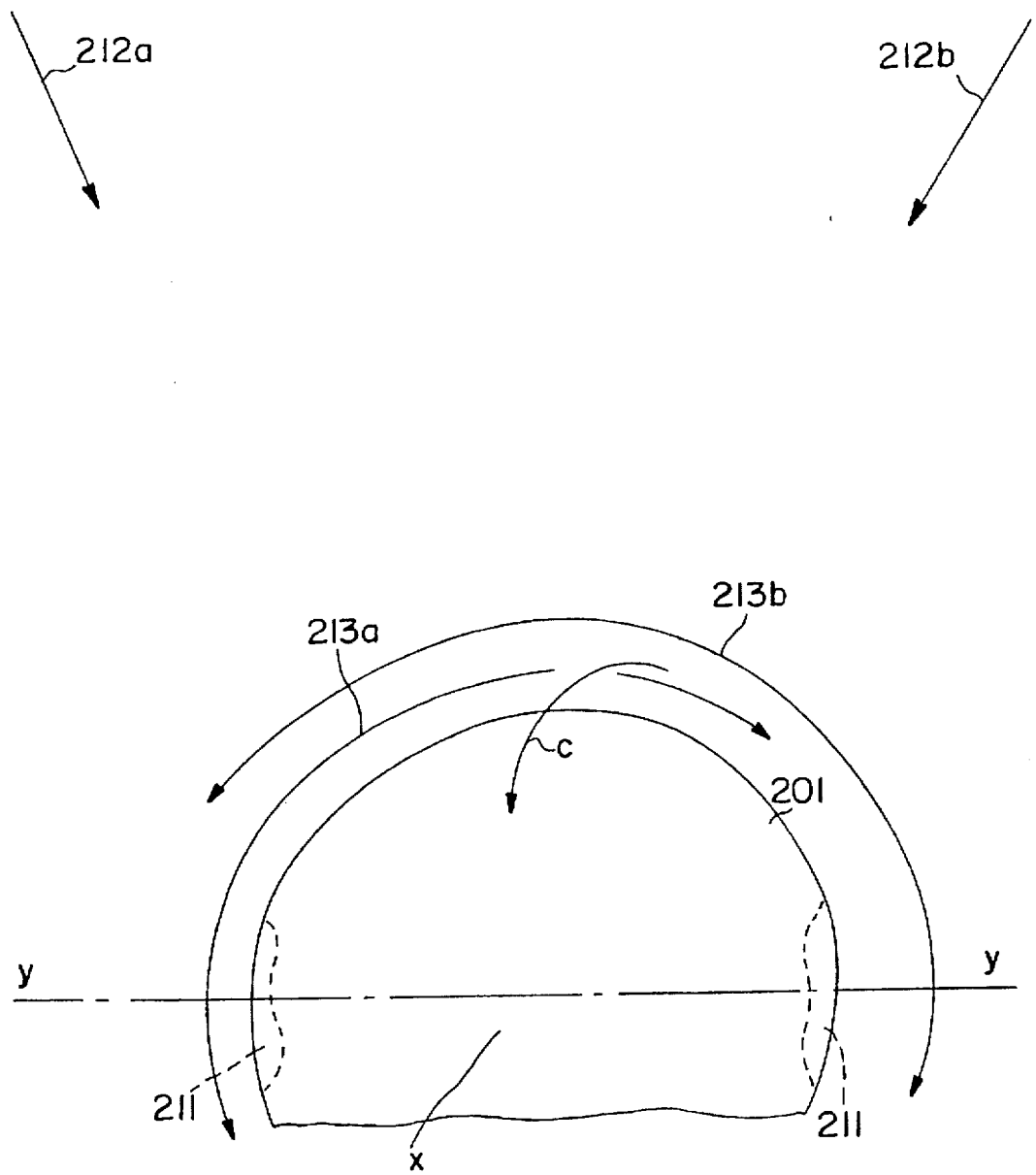
FIG. 12 is a diagrammatic representation of a dual-scanning arrangement providing for improved detection of abnormalities on side regions of a product, relative to the direction of product advance.

Adverting now to FIG. 12, there is indicated the use of dual scanners and optical sensors 212a and 212b, each operating at an angle with respect to the X and Y axes as identified in FIG. 12, so as to give a better view of the end areas 211 of the product 201, these representing the regions round the points of notional emergence of the nominal axis of rotation y—y of the product in the direction of arrow C. In this manner, enhanced inspection of the sides of the product relative to the direction of product advance is provided. Correlation of the information returned by the respective angled scanning and optical devices with the other parameters of product drive and rotation enables the region being viewed to be specifically identified, as well as the nature of any defect revealed by the signals returned. Thus effectively a larger area of product is scanned by use of a second sensor in this manner. Because the second sensor is aligned at a different angle with respect to the object scanned as compared with the first sensor, the signals at the second sensor 212b represent the scan of a different peripheral portion 213b of the product from that 213a monitored by the first sensor 212a, in terms of the scanning direction. The effect therefore is that each of the two sensors inspects a particular region unique to that sensor, but there is also a common area which is scanned by both sensors. When this system is used in conjunction with two light beams of different wavebands, additional information may be retrieved from the system, in that the common area is inspected by signals of two different wavebands. Still further scanners operating at still additional wavebands may also be used in the system of the invention, and there is no limitation to single or dual arrangements for a particular group of products. Multiple scanner and sensor arrangements may also be located side by side, rather than angularly displaced as in FIG. 12, so that each scanner scans substantially the same product portion.

In addition to an aligned array of scanners being provided across the conveyor width as required to facilitate coverage of a wide belt having regard to the limited length of scan of an individual scanner, further scanners and sensors may also be disposed in succession in the direction of product advance.

Thus in a further variant in the invention, different wavelengths may be used for two scanning systems, and/or these scanning systems may be spaced apart in the direction of travel, so that results may be derived which are spaced apart in time but are not otherwise coordinated. This decision making may involve weighting the results of inspections at different stages of the sorting operation according to a diversity of criteria.

Figure 13:
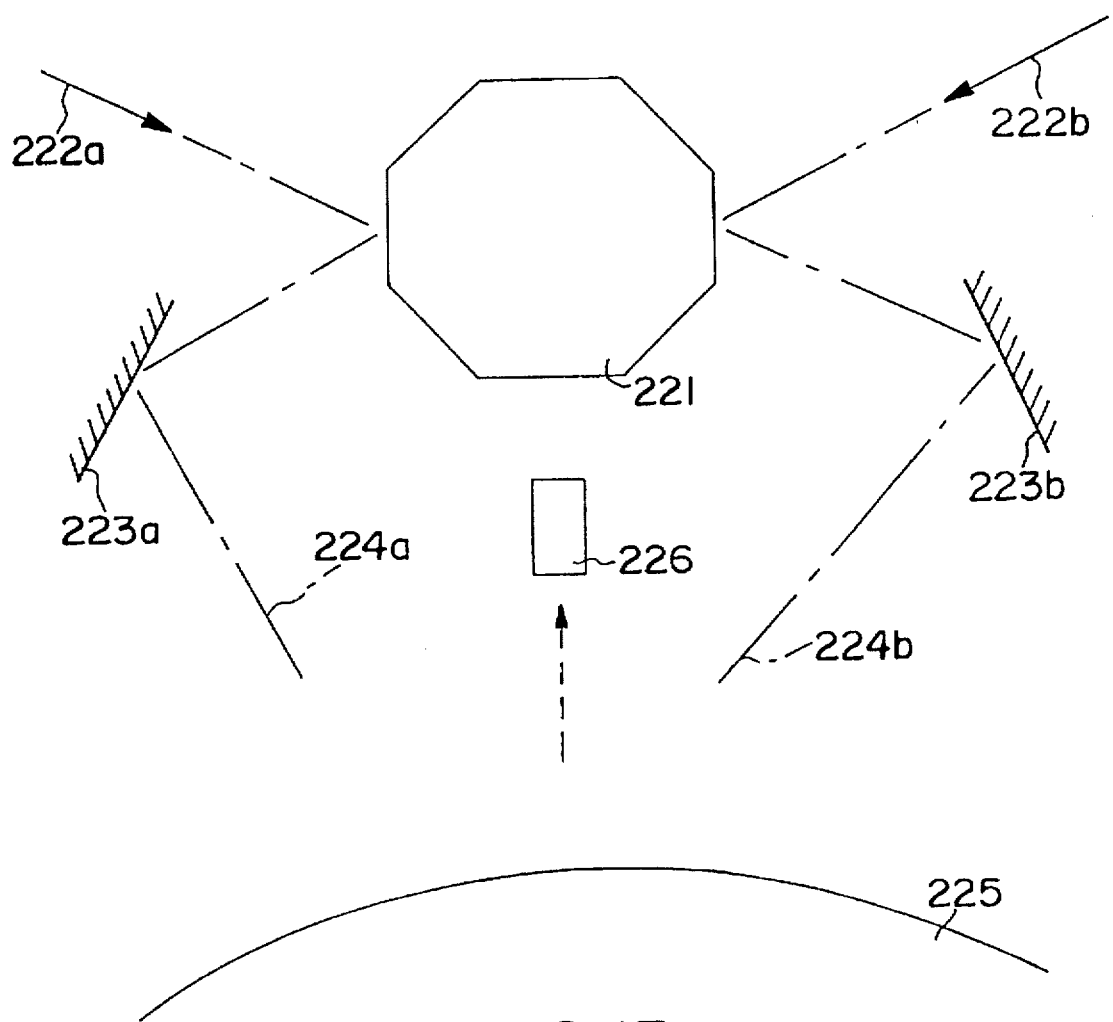
FIG. 13 shows a modification of a system in accordance with the invention in which two scanning beams cooperate with a single sensor or detector.

FIG. 13 shows an arrangement in which synchronised dual scanning is used. Angled scanning from scanners 222a and 222b synchronised by a single rotating mirror 221 and static mirrors 223a and b provides for the successive movement of individual angled beams across the surface of an object 225, with vertical sensing of the returned light signals by centrally located sensor 226.

Analysis effected in this manner, namely placement of the sensor 226 at a location other than adjacent to the scanners 222a and b facilitates the determination of additional information about surface texture and/or surface and sub-surface defects in a product monitored in accordance with the principles of the invention.

Irrespective of the imaging technique, therefore and of whether the signal sensing is effected by a sensor or other detector means positioned adjacent to the light source or arranged at an angular displacement relative to the light beam, an image is built up, an analysis is conducted, and a decision is made. By analysing the image, defining the number of objects, the outlines of the objects, their sizes, the number and sizes of the defects, their severity, and also effecting any other analysis required, a decision is made whether to accept or reject the object.

Referring now to FIGS. 14 to 16 and also again to FIGS. 5, 6 and 7, an inspection device according to the invention in a further arrangement consisting of a monitoring or sorting system embodying the principles of the invention for particular application to the separation of vegetable product such as potatoes from extraneous matter such as dirt and stones comprises a series of light sources 11 each itself defined by a series of light emitting diodes (LEDs) 31a, 31b, 31c and 31d emitting pulsed infrared light which is projected by means of a lens system 33 towards and onto the end region of belt 1, FIG. 7. In operation, the belt 1 carries randomly spaced products 2, FIG. 7, having different properties. Each LED 31 is sequentially pulsed in the sequence indicated by the identifications 1 to 10 marked against each LED in FIG. 14, thus producing a line scan across the width of the belt 1. The scanning rate is selected for optimal retrieval of useful information. Both directly reflected light from the objects and diffused or scattered light transmitted through the objects are then detected by a series of detector system units or sensors 38, each of which includes three separate adjacently positioned detector elements, 14, 15, 16, as already described, FIGS. 5 and 6. As shown in FIG. 16, in particular, the detectors 14, 15, 16 are each of elongate generally rectangular configuration in planar view and extend generally parallel to one another. In each detection or sensor system unit 38, the light returned from the objects is imaged by means of a lens system 35 onto an image plane, through a filter 36. The target points for the light beams provided by the LEDs 31a, 31b, 31c and 31d are designated in FIG. 15 by references 32a to 32d. The arrangement of the LEDs in the light source units 11 is such that these spots of light define a uniform sequential pattern extending across the product inspection zone, as designated by the sequence numbers 1 through 10 applied to the spots of light and also indicated on FIG. 15. The detectors 14, 15, 16 are positioned in each case on the image plane of the detector units 38 in such a way that the central detector 14 of each unit sees the direct reflections from a particular sequence of target spots 32. The spacing of the LEDs 31 and detectors 14, 15, 16 from the inspection plane 41, (FIG. 14), on which plane the target spots of light 32 are optimize, is selected to optimized also the field of view. The boundaries of the field of view of the detector or sensor units 38 are designated by references 37 in FIG. 15.

Vegetable matter in particular exhibits the characteristic of scatter and diffused light transmission, as already described. The two outside detectors 15, 16 are positioned so that they see only the diffused transmitted or scattered light which has passed through the vegetable material and emerged from it outward of the position from which the directly reflected light is returned, i.e. away the point of impingement 12 of the light beam 13 (FIGS. 5, 6 and 16). In other words therefore, the central detector 14 receives the direct reflection while the outside detectors 15, 16 are responsive only to light returned to the detector by way of the diffused scattered light transmission path through the material to each side of the central reflecting region 12 (FIGS. 5 and 6). This light emanates from the product in the diffused light region 13, which is as it were lit up from the interior by the scattered light diffusing through the material of the product undergoing inspection. The ratio of the diffused scattered transmission to the reflected light determines whether the particular object under inspection is retained or rejected.

Figure 14:
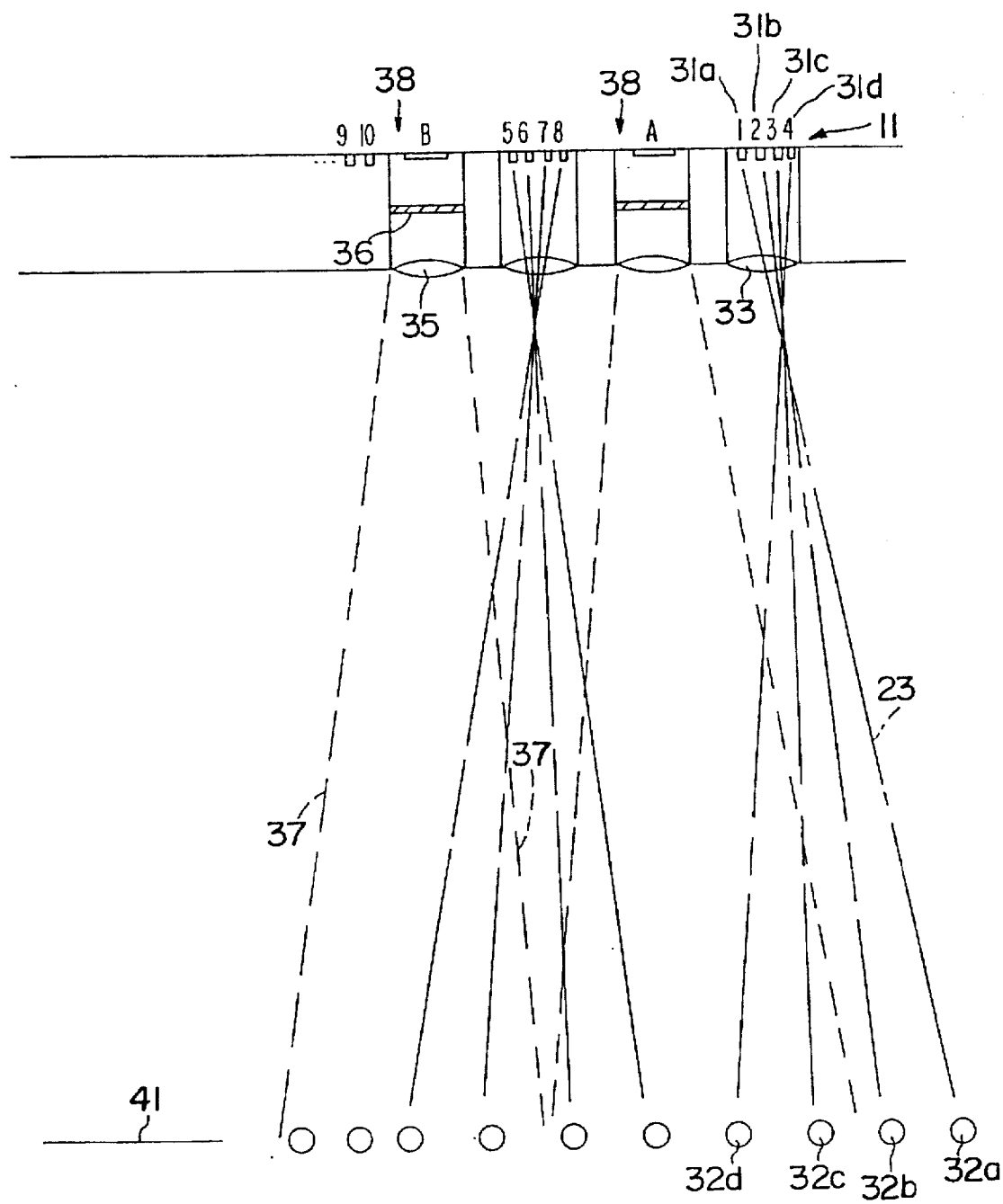
FIG. 14 is a view looking along the belt of a sorting device of the kind shown in FIG. 7 of a variant of light emitting and detecting sorting system in accordance with the invention.
Figure 15:
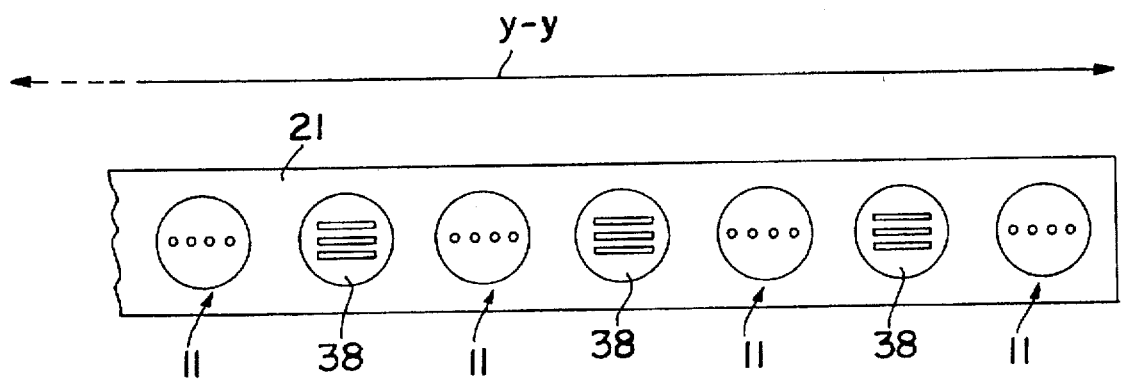
FIG. 15 is a top view of LEDs and detectors of the system in accordance with the invention as shown in FIG. 14.
Figure 16:
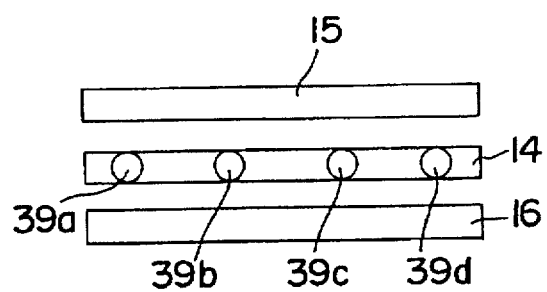
FIG. 16 is a representation of the projected field of view of the detector arrangement of FIGS. 14 and 15.

Referring in further detail to FIGS. 14 through 16, the arrangement is such that a detector or sensor set 38 identified by sequence reference "A" (FIG. 14) is selected by the circuitry to receive information during the period while the LEDs 31 identified by the energisation sequence numerals 3, 4, 5 and 6 are sequentially turned on and off. Information received by this detector or sensor set is then analysed. Detector or sensor set "B" is then selected, while LEDs 7, 8, 9 and 10 are sequentially turned on and off, and the information from set "B" is also analysed in turn. This sequence is repeated for as many detector or sensor and LED sets as are part of the whole system across the width of the belt.

Analysis of information from any one of the LEDs takes place as follows:

The central detector element 14 of the detector set has two functions, namely:

(a) It determines whether an object is present, and
(b) It produces a signal proportional to the reflected light in its field of view.

At the same time detector elements 15 and 16 produce a signal proportional to the transmitted diffused or scattered light in their fields of view, i.e. the light passing through the interior or material of the object under consideration and becoming evident at the surface of the object in the region 13 (FIGS. 5 and 6) to each side of the impingement point of the illuminating beam 23.

An object is established as being present when the signal level of detector 14 exceeds a predetermined or threshold value.

The pulses of light incident on each of the detectors 14, 15, 16, which are suitably photo-detectors, are then amplified and synchronously demodulated to give a DC type signal representing the presence of an object and whether it is for example a potato, in the present application. If the object is not a potato, a reject signal is generated. The reject signal is processed by delay circuitry to compensate for the time differential between the near instantaneous determination of the material nature of the object and the time-lagging physical removal of the object from the material stream. Stretch circuitry is then applied to the lengthened duration of the delayed reject signals so that account is taken of the inability of the physical removal apparatus 4 (FIG. 7) to act instantaneously in response to electrical signals.

The filters 36 are located in front of the detectors 14, 15, 16 within the detector units 38 to narrow the spectrum of incident daylight or ambient light to the frequencies being used, thus increasing the signal to noise ratio of the detectors.

LEDs are given by way of exemplary light sources 31 only. They represent only one possible type of light source. Also, LEDs of a diversity of characteristics may be used, or alternatively they may be substituted by a scanning laser or any other suitable device.

The light sources 31 may operate on a monochromatic basis and the wavelength of the illumination may be selected to enable the establishment of the presence or absence of certain specific characteristics in the product. For potatoes, the inspection operation may be conducted in the infrared region, but for tomatoes or other like products, alternative portions of the spectrum and specific individual wavelengths may be preferred, e.g. 660 nm for tomatoes.

Figure 17:
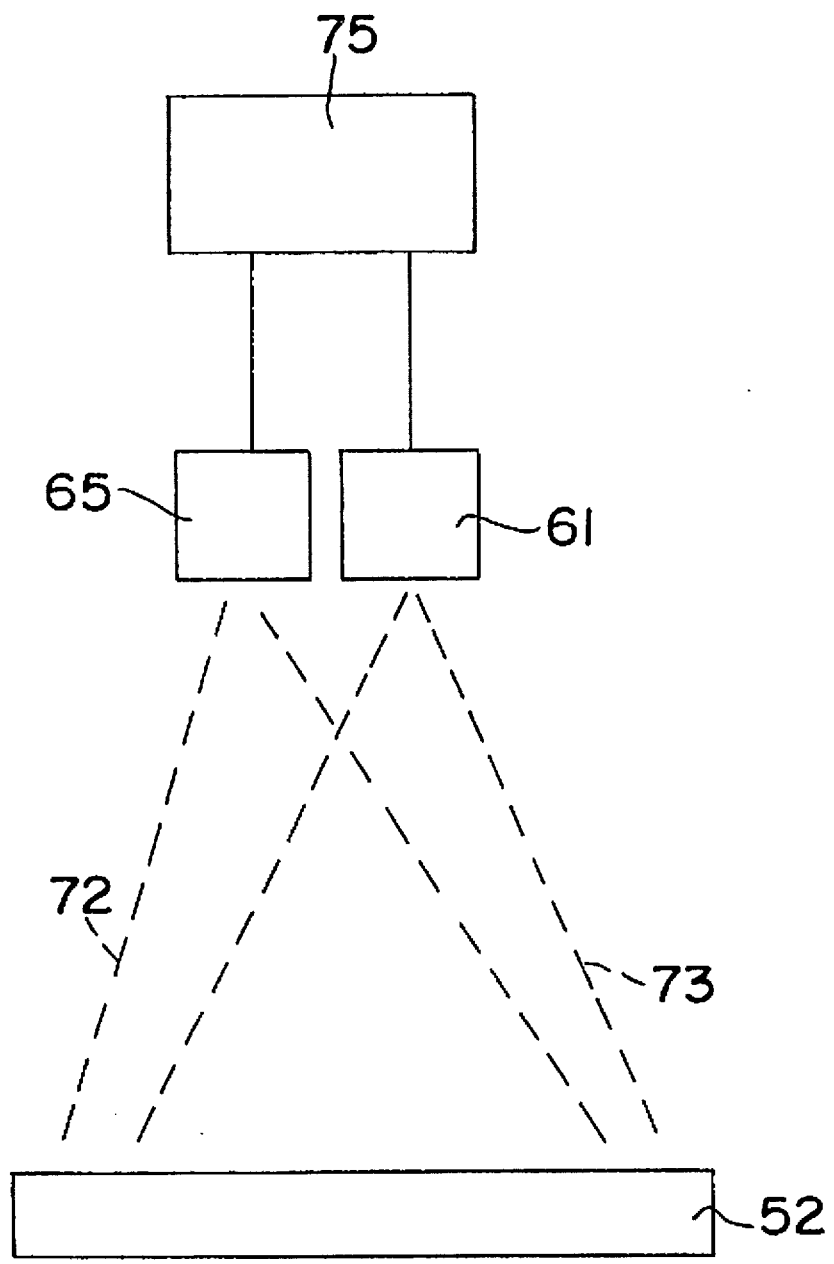
FIG. 17 is a diagrammatic representation of a system in accordance with the invention in which a laser scanner and associated array camera are used.

A still further embodiment of a system in accordance with the invention is shown in schematic representation in FIG. 17. In the arrangement shown in diagrammatic representation only, a laser scanner 61 directs a light beam in a scanning pattern onto an object 52, the boundaries of scanning for the laser light beam being indicated by reference 73. Both directly reflected and diffused light returns to an array sensor camera 65 along paths with limits designated by reference 72. The scanning operation of the laser device 61 and the interpretation of the reflected and diffused light received by the camera 65 are accomplished by an electronic control and interpretation system, designated schematically by reference 75.

Figure 18:
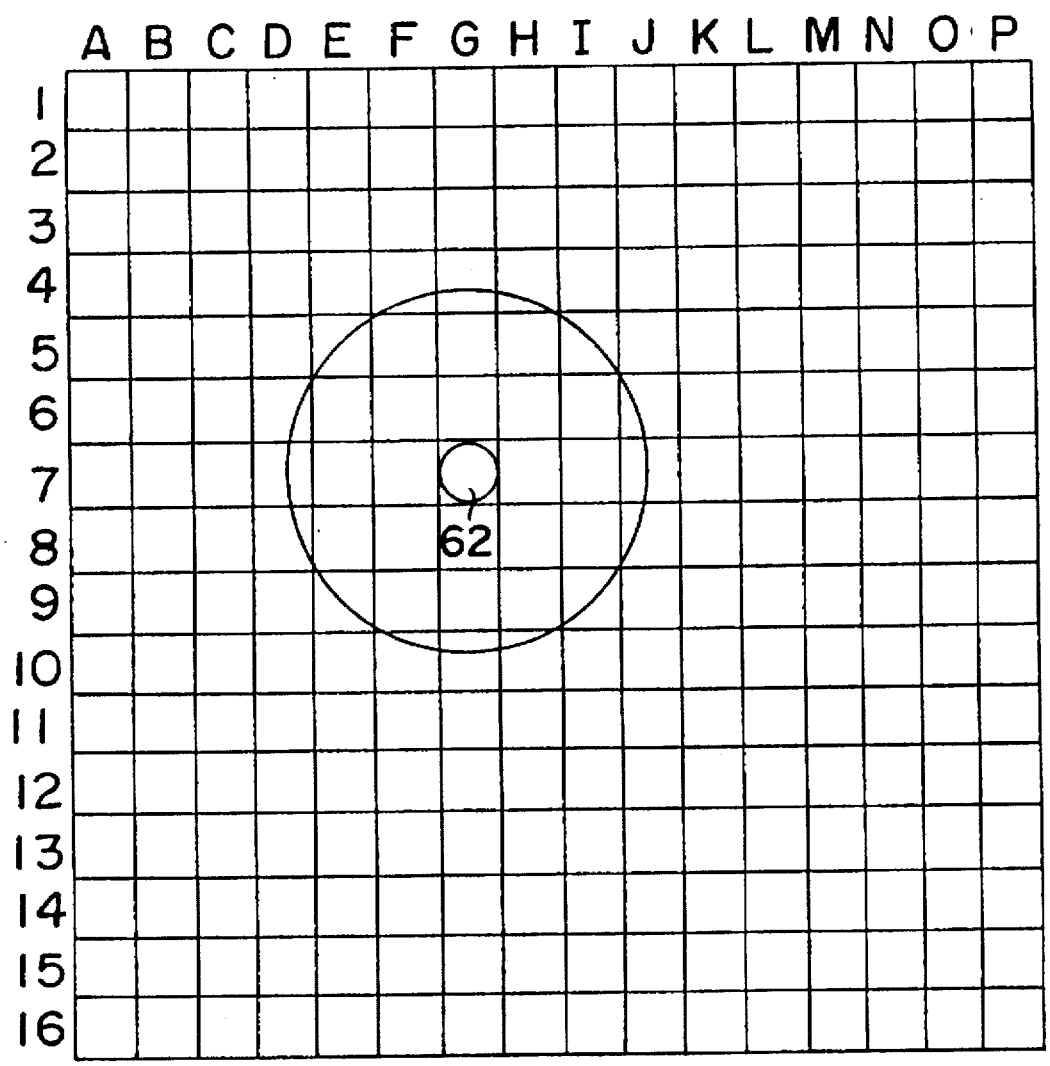
FIG. 18 is a diagrammatic representation of an array analysis procedure applicable in operation of the system of FIG. 18.

A manner of functioning of the invention in this embodiment is shown in FIG. 18. A grid of 256 pixel locations, as seen by the array camera, is designated by rows 1 to 16 and columns A to P. The laser scanner 61 traverses this grid in a pre-programmed manner under the direction of the control apparatus 75. An instantaneous laser spot position is designated by reference 62, grid reference G7. When the laser is directed to this grid reference spot, light returned to the camera array receptors by object 52 at camera grid location G7, is interpreted as a direct reflection and camera grid location G7 identifies the received light signal accordingly, this information being suitably-interpreted by unit 75 to provide output information. At the same time, in the exemplary arrangement of FIG. 18, a number of further grid reference position locations surrounding G7 are also selected as detectors at this particular moment and light received within these further pixel locations is interpreted as diffused transmitted light, returned in the manner previously described in connection with earlier embodiments. According as the laser spot position moves from grid square to grid square, i.e. from pixel to pixel, the substantially circular group of detectors surrounding the instantaneous laser spot position is reorganized so that a comparable group of detectors to those surrounding spot position G7 is always selected to determine the diffused light returned from further instantaneous laser spot positions. In other words, as the laser spot travels, so also does the selected detector area by virtue of which the directly reflected light and the diffused transmitted light is received.

In this adaptation of the system of the invention in which an array type camera is used, groups of pixels are therefore energized at any one time. The camera grid and the laser scanning grid are linked and synchronized by electronic unit 75. As the laser spot traverses the grid, the camera grid is at the same time activated appropriately so that the central pixel of the active area corresponds to the return of the directly reflected light, while the surrounding pixels detect the diffused light energy. It will be apparent that the entire camera grid array is not active at any one time, and that only a relatively limited number of pixels are activated, primarily for ease of data processing. As shown in FIG. 18, approximately two pixels radially outward from and surrounding the instantaneous laser spot position are selected at any one time, but a greater or a lesser number of surrounding pixels may likewise be selected within the ambit of the present invention, depending on the level of processing analysis available and required.

In a development of the invention, in which it is applied to ripeness gradation, the wavelength of the light to which the product is exposed may be varied and the positioning of the detectors within the field of view may also be adjusted, so that, depending on the product, internal ripeness as distinct from apparent surface ripeness may be identified. Determination of internal ripeness enables the likely progress of the product towards full maturation to be assessed. The system of the invention therefore enables mechanization of the process of establishing internal ripeness, which has not hitherto been possible under factory conditions at high capacities. It therefore facilitates product gradation with reference to the ripeness of an immature product.

The invention may be further applied to detecting characteristics of a diversity of types of light transmitting materials, whether organic or inorganic. In particular, the system of the invention may be applied to the disclosure of information concerning internal properties of living matter, both animal and human. By selecting the wavelength of the scanning light to which the object is disposed and detecting the diffused scattered transmitted light in a selectively variable and optionally relatively wide area around each pixel of illumination, information may be built up about the internal structure of an object or material. This information may serve as the input for a visual display unit, and be correlated to provide meaningful display representations on such display systems. Variation of the wavelengths of the illuminating light makes it possible to view and image various components of the internal structure of the object. For example, in the case of living organic structures, the invention enables information and imaging of vein structure, muscle tissue, bones, tumors and the like to be detected by external examination without exposure to harmful media or radiation, and, by application of computer-based enhancement techniques, to be translated into visual displays for study and analysis by appropriately skilled users.

Thus in a system according to the invention, the substantially total dependence on reflected light which is a feature of many known systems is avoided. Likewise any dependence on the through transmission of light is also avoided. In the system of the invention, significant changes occur in the signals detected when the spot of light directed onto the product is initially near the defect and when it is then traversed onto and through the defect. When the light is beamed onto a region near a defect, the directly reflected signal is of relatively high value, and there is also good transmission of scattered light to one side of the spot, in the region where the product is good, but poor transmission through the product on the damaged or defective side. Significant information is therefore available from illumination of the product in the system according to the invention according as a scanning operation is conducted across and through a defective area. The scattered light detected in the system of the invention is light which is distributed or redistributed internally within the material of the product by transmission through the substance or material of the product or object. The nature of this returned or scattered light is perceptibly different from that provided by a reflection-only type system or by a system in which through transmission of light is monitored.

The system of the invention is not limited to the use of merely one or two spectral bands of radiation. Thus the system of the invention may operate with a multiplicity of color bands, since the technique imposes no constraint on the type of light emission and detection equipment used. Furthermore, the system of the invention is especially suited to the detection and analysis as to their nature of defects of small dimensions.

Another advantage of the invention is its ability to generate additional information about a product by the deployment of additional imaging or monitoring systems, functioning in conjunction with the main light monitoring aspect provided in the system embodying the basic principles of the present invention, in which, in particular, differential assessment of the levels of directly-reflected and diffused or scattered light is preferably effected. Thus additional decision making information may be provided and a final decision on whether to accept or reject product developed by weighting of individual decisions from different sources of information.

The system is particularly applicable to whole tomatoes, and also to diced tomatoes, peeled tomatoes, and other fruit and vegetable products, as well as processed products such as creams, slurries and purees. Thus the invention is not suited merely to the inspection of objects per se but also to the inspection and monitoring of suitable materials in general, in particular, to materials and in a wider sense than those embodied in a substantially rigid or defined physical object. In particular, the invention may be applied to the inspection of organic material in general, including living organic material with a view to the assessment of, for example, adverse medical or veterinary problems in such living tissue. In application to inorganic material, the invention may in particular, be applied to the identification of internal cavities or voids in plastics or rubber materials.

We claim:

1. An information gathering system comprising:
   (a) means for directing at least one light beam at a surface of a material having internal light-scattering properties for which information is required in respect of at least one specified characteristic of the material, to impinge upon a target region on said surface of said material,
   (b) means for effecting scanning displacement of said at least one light beam relative to said surface of said material so that said target region comprises one of a succession of target regions,
   (c) means for detecting reflected light returned from said target region,
   (d) means for detecting internally-scattered light emanating from a region of said surface of said material other than said target region, said region other than said target region being one of substantially adjacent and or continuous with said target region,
   (e) means for deriving a signal indicative of said at least one specified characteristic of the material by analysis of the levels of said reflected light and said emanating light during said scanning displacement, and
   (f) means for effecting displacement of said surface of said material relative to said at least one light beam in a direction substantially at right angles to said direction of scanning displacement, wherein
      (i) a speed of said scanning displacement is determined in conjunction with a speed of displacement of said surface of said material so that a succession of scanning displacements of said at least one light beam relative to said surface of said material is achieved, and (ii) said signal deriving means comprises memory means to enable build-up of image data for said surface from the levels of said reflected light and said emanating light during each of said succession of scanning displacements to provide said signal indicative of said at least one specified characteristic of the material by analysis of said image data.

2. An information gathering system according to claim 1, wherein said signal deriving means comprises logic means for effecting said analysis of said image data.

3. An information gathering system according to claim 2, wherein said logic means is adapted to distinguish between a plurality of abnormalities or defects of said material to provide said signal indicative of said at least one specified characteristic of the material.

4. An information gathering system according to claim 3, wherein said signal deriving means is adapted for analysis of said image data for derivation of at least one of size and shape characteristics of said material.

5. An information gathering system according to claim 4, wherein said signal deriving means is adapted to provide said signal indicative of said at least one specified characteristic of the material at least from one of the intensity of said reflected light and said emanating light, and by comparison of the relative levels of said reflected light and said emanating light at each of said succession of target regions for each of said succession of scanning displacements.

6. An information gathering system according to claim 1, wherein said signal deriving means is adapted to provide said signal indicative of said at least one specified characteristic of the material at least from one of the intensity of said reflected light and said emanating light, and by comparison of the relative levels of said reflected light and said emanating light at each of said succession of target regions for each of said succession of scanning displacements.

7. An information gathering system according to claim 1, wherein:

(i) said light beam directing means comprises means for directing each of at least two light beams of different wavelengths at said surface to each impinge upon a respective target region on said surface; and (ii) said scanning displacement effecting means is adapted to effect scanning displacement of each of said at least two light beams relative to said surface so that each said target region comprises one of a respective succession of target regions and at least some of each of said successions of target regions define a common area for inspection by each of said at least two light beams of different wavelengths.

8. An information gathering system according to claims 7, wherein said signal deriving means is adapted to provide said signal indicative of said at least one specified characteristic of the material at least from the intensity of said reflected light and said emanating light and/or by comparison of the relative levels of said reflected light and said emanating light at each of said successions of target regions defining said common area.

9. An information gathering system according to claim 1, wherein said light detecting means comprises a plurality of linear photosensitive detectors aligned in said scanning direction.

10. An information gathering system according to claim 1, comprising means for providing to said signal deriving means, at least one additional input of information derived from another monitoring technique.

11. An information gathering system comprising:

(a) means for directing at least one light beam at a surface of a material having internal light-scattering properties for which information is required in respect of at least one specified characteristic of the material, to impinge upon a target region on said surface of said material during passage of said material through an inspection zone, (b) means for effecting scanning displacement of said at least one light beam relative to said surface of said material so that said target region comprises on of a succession of target regions, (c) means for detecting reflected light returned from said target region, (d) means for detecting internally-scattered light emanating from a region of said surface of said material other than said target region, said region other than said target region being one of substantially adjacent to and continuous with said target region, (e) means for deriving a signal indicative of said at least one specified characteristic of the material by analysis of the levels of said reflected light and said emanating light during said scanning displacement, and (f) means for effecting displacement of said surface of said material through said inspection zone relative to said at least one light beam in a direction substantially at right angles to said direction of scanning displacement, wherein (i) a speed of said scanning displacement is determined in conjunction with a speed of displacement of said surface of said material so that a succession of scanning displacements of said at least one light beam relative to said surface of said material is achieved, (ii) said signal deriving means comprises memory means to enable build-up of image data for said surface from the levels of said reflected light and said emanating light during each of said succession of scanning displacements to provide said signal indicative of said at least one specified characteristic of the material by analysis of said image data, (iii) said means for effecting displacement of said surface of said material comprises a conveyor for advancing said material to an end region of the conveyor at which said material leaves the conveyor in a freefall trajectory, and (iv) said inspection zone is defined by a portion of said freefall trajectory.

12. An information gathering system according to claim 11, wherein said signal deriving means comprises logic means for effecting said analysis of said image data.

13. An information gathering system according to claim 12, wherein said logic means is adapted to distinguish between a plurality of abnormalities or defects of said material to provide said signal indicative of said at least one specified characteristic of the material.

14. An information gathering system according to claim 13, wherein said signal deriving means is adapted for analysis of said image data for derivation of at least one of size and shape characteristics of said material.

15. An information gathering system according to claim 14, wherein said signal deriving means is adapted to provide said signal indicative of said at least one specified characteristic of the material at least from one of the intensity of said reflected light and said emanating light, and by comparison of the relative levels of said reflected light and said emanating light at each of said succession of target regions for each of said succession of scanning displacements.

16. An information gathering system according to claim 11, wherein said signal deriving means is adapted to provide said signal indicative of said at least one specified characteristic of the material at least from one of the intensity of said reflected light and said emanating light, and by comparison of the relative levels of said reflected light and said emanating light at each of said succession of target regions for each of said succession of scanning displacements.

17. An information gathering system according to claim 11, wherein:
   (i) said light beam directing means comprises means for directing each of at least two light beams of different wavelengths at said surface to each impinge upon a respective target region on said surface; and
   (ii) said scanning displacement effecting means is adapted to effect scanning displacement of each of said at least two light beams relative to said surface so that each said target region comprises one of a respective succession of target regions and at least some of each of said successions of target regions define a common area for inspection by each of said at least two light beams of different wavelengths.

18. An information gathering system according to claim 17, wherein said signal deriving means is adapted to provide said signal indicative of said at least one specified characteristic of the material at least from one of the intensity of said reflected light and said emanating light, and by comparison of the relative levels of said reflected light and said emanating light at each of said successions of target regions defining said common area.

19. An information gathering system according to claim 11, wherein said light detecting means comprises a plurality of linear photosensitive detectors aligned in said scanning direction.

20. An information gathering system according to claim 11, comprising means for providing to said signal deriving means, at least one additional input of information derived from another monitoring technique.

21. An information gathering system according to claim 11, wherein said light-beam directing means, said scanning displacement means, said reflected light-detecting means and said internally-scattered light detecting means are comprised in an inspection device extending transversely substantially across the entire path of advance of said material on said conveyor.

* * * * *